US012788727B2

(12) United States Patent
Ashraf et al.

(10) Patent No.: US 12,788,727 B2
(45) Date of Patent: Nov. 10, 2026

(54) DEVICES AND METHODS FOR SELECTIVELY ACCESSING TISSUE

(71) Applicant: Rutgers, The State University of New Jersey, New Brunswick, NJ (US)

(72) Inventors: Ali Ashraf, McAllen, TX (US); Stephen Dalton McLaughlin, Princeton, NJ (US); Mehdi Javanmard, Princeton Junction, NJ (US); Francois Berthiaume, Metuchen, NJ (US); Aaron D. Mazzeo, Edison, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 564 days.

(21) Appl. No.: 18/496,604

(22) Filed: Oct. 27, 2023

(65) Prior Publication Data

US 2024/0139118 A1 May 2, 2024

Related U.S. Application Data

(60) Provisional application No. 63/381,500, filed on Oct. 28, 2022.

(51) Int. Cl.
*A61K 9/70* (2006.01)
*A61M 37/00* (2006.01)
*G16H 40/60* (2018.01)

(52) U.S. Cl.
CPC ......... *A61K 9/703* (2013.01); *A61M 37/0092* (2013.01); *G16H 40/60* (2018.01)

(58) Field of Classification Search
CPC .... A61K 9/703; A61M 37/0092; G16H 40/60
See application file for complete search history.

(56) References Cited

U.S. PATENT DOCUMENTS 10,286,198 B2 * 5/2019 Dang .................... A61K 9/0009
2004/0106914 A1 * 6/2004 Coppeta ............ A61M 37/0015 604/892.1

FOREIGN PATENT DOCUMENTS

WO 2019190596 A1 10/2019

OTHER PUBLICATIONS

A. Vega-Flick, et al., "Vibrations of micron-sized fluid membranes induced via pulsed laser excitation," Journal of Fluids and Structures, Journal of Fluids and Structures 81 (2018) pp. 58-68, May 8, 2018.

Jason Li, et al., "Clinical Opportunities for Continuous Biosensing and Closed-Loop Therapies," Trends in Chemistry, Apr. 2020, vol. 2, No. 4, pp. 319-340.

* cited by examiner

*Primary Examiner* — Rebecca E Eisenberg
*Assistant Examiner* — Gabriella E Burnette
(74) *Attorney, Agent, or Firm* — Hamilton, Brook, Smith & Reynolds, P.C.

(57) ABSTRACT

Devices and methods for selectively accessing tissue for sensing or drug release are provided. A device includes an array of wells formed in a substrate supporting a plurality of membranes. Each membrane is disposed at a well opening of one of the wells of the array. The device further includes an actuator and electronics configured to control the actuator to supply a vibration through the substrate. The supplied vibration is configured to selectively rupture one of the plurality of membranes at a defined timepoint to selectively give access to tissue through a well opening.

22 Claims, 43 Drawing Sheets
(41 of 43 Drawing Sheet(s) Filed in Color)

600

1800

2000

2100

2600a

2600b

2600c

2600d

2600e

2800a

2800b

2800c

2800d

2800e

2900

DEVICES AND METHODS FOR SELECTIVELY ACCESSING TISSUE

RELATED APPLICATION

This application claims the benefit of U.S. Provisional Application No. 63/381,500, filed on Oct. 28, 2022. The entire teachings of the above application are incorporated herein by reference.

GOVERNMENT SUPPORT

This invention was made with government support under Grant No. FA8650-20-2-7032 from the Defense Advanced Research Projects Agency. The government has certain rights in the invention.

BACKGROUND

Various biomarkers can be indicative of wound healing stages. For example, concentrations of the cytokines TNFα and IL-1 are known to peak during an Inflammation Phase (e.g., from the time of injury to about 6 days), while other proteins, such as SDF-1α, peak during a Proliferation Phase (e.g., from about 3 days to several weeks from injury). Wound closure is known to coincide with an increase in TGFβ during a Remodeling Phase (e.g., from about 7 days to two years or more from injury). There is a need for improved methods of monitoring wound-healing biomarkers.

Examples of existing time-release technology, such as for sensing and drug delivery, include trigger-released nanoparticles, dissolvable tablets, acoustic activation of micelles, thermal release, and membrane covers configured to melt to expose chambers of a device over time. There is a need for improved, biocompatible time-release technology.

SUMMARY

Devices and methods are provided that can provide for timed biosensing, timed drug delivery, or both. Such devices and methods can employ mechanical vibrations to rupture membranes and permit fluid flow into receptacles of a wearable device, which can be useful for a variety of applications, including, for example, monitoring wound healing and releasing therapeutics over time. By sensing a concentration of, for example, wound-healing biomarkers, a wound healing stage can be determined and the recovery progression process can be monitored, which can assist with informing treatment. It can be desirable to monitor for such biomarkers on a periodic basis without aggravation to the wound and without requiring active monitoring steps on the part of the user. The devices can be adapted to be worn on the body, for example, on skin, and/or can be included in a bandage to provide for wound monitoring while simultaneously promoting healing. The device can alternatively be adapted to be implanted within the body, such as, for example, as a component part of a surgical mesh implant.

A device to selectively access tissue for sensing or drug release includes an array of wells formed in a substrate supporting a plurality of membranes. Each membrane is disposed at a well opening of one of the wells of the array. The device further includes an actuator and electronics configured to control the actuator to supply a vibration through the substrate. The supplied vibration is configured to selectively rupture one of the plurality of membranes at a defined timepoint to selectively give access to tissue through a well opening.

The rupturing of the membrane can break an interface between the tissue and the well at which the membrane is disposed. The membranes can comprise a material including, for example, graphene oxide, polymer thin film, metal, ceramic, cellulose paper, or a combination thereof. A membrane can comprise a sheet, e.g., a thin sheet, of liquid-proof material configured to resonate at a defined frequency when exposed to the vibration. The defined frequency of one membrane of the array may differ from that of other membranes in the array.

The supplied vibration can cause the plurality of membranes to accumulate different degrees of damage over time. A membrane may be of a shape that is adapted to respond to the vibration according to a frequency and direction of the vibration. For example, a membrane can be rectangularly-shaped, triangularly-shaped, circularly-shaped, polygonal-shaped, or oblong-shaped. The device can include two or more actuators, such that each actuator can supply vibrations having different frequencies, originating from different directions with respect to the array, or a combination thereof. The device can include an external power source configured to drive the electronics, the actuator, or both.

Porous membranes can be included, in addition to the rupturable membranes, to prevent debris from transferring in or out of the device. For example, it may be desirable to prevent ruptured membrane particles from entering the blood stream of a subject having a wound at which the device is disposed. In another example, it may be desirable to permit fluid, such as blood or wound fluid, emanating from the tissue to entire the wells of the array, but to prevent larger particles that may interfere with sensor operation from entering the well. A porous membrane can cover each rupturable membrane. For example, a defined porous membrane can be associated with each rupturable membrane. Alternatively, a porous membrane layer can be included that extends across the array of wells.

Micro-channels can be included in the device. For example, each well of the array can have an associated micro-channel configured to guide fluid into the well from the tissue.

A drug, a sensor, or a combination thereof can be encapsulated in a well. The device may be wearable or implantable. For example, at least a portion of the substrate can be configured to be positioned at a biological surface, such as in a bandage-like format or as a component of a bandage. Alternatively, at least a portion of the substrate can be configured to be implanted into a biological tissue.

A method for selectively accessing tissue for sensing or drug release includes providing an array of wells formed in a substrate supporting a plurality of membranes. Each membrane is disposed at a well opening of one of the wells. The method further includes controlling an actuator to supply a vibration through the substrate, the supplied vibration selectively rupturing one of the plurality of membranes at a defined timepoint to selectively give access to tissue through a well opening.

Rupturing of a membrane can include breaking an interface between the tissue and a well. Supplying the vibration to the substrate can include providing varying degrees of accumulated damage over time to each of the plurality of membranes. Supplying the vibration to the substrate can include supplying the vibration according to a frequency, a direction, or a combination thereof for the selective rupture of the one of the plurality of membranes.

The method can further include preventing debris from the rupture of the one of the plurality of membranes from reaching the tissue. The method can further include guiding fluid from tissue into a well associated with the well opening via a micro-channel.

The method can include exposing the tissue to a drug encapsulated in a well associated with the well opening, exposing a sensor encapsulated in the well associated with the well opening to fluid from the tissue, or a combination thereof.

The method can include positioning at least a portion of the substrate at a biological surface or implanting at least a portion of the substrate into a biological tissue.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

DETAILED DESCRIPTION

A description of example embodiments follows.

Biosensing and drug release can each require activation at specified times. Devices are provided that include an array of wells, or receptacles, that can be individually, selectively exposed to tissue. Such methods and devices can employ mechanical vibrations to rupture membranes disposed at each of the wells of the array, thereby permitting fluid flow into the wells or otherwise yielding access to tissue. The membranes of the array can be ruptured in an intended sequence, such that membranes at different locations within the array are ruptured at different times. Such timing can be programmable based on an amplitude and/or frequency of vibration applied to the substrate defining the array of wells. For example, the applied vibration can excite the membrane and/or the surrounding substrate material at its resonant frequency to effect rupture of the membrane while other membranes are unaffected or are affected by different rates of cumulative damage.

A sequence for membrane ruptures at different well locations within the array can be controlled by any or all of the following: varying an amplitude and/or frequency of vibration, varying a material, shape, and/or structure of the membranes disposed at the wells, varying a direction of applied vibration(s), varying a well shape and/or size, varying an overall shape or configuration of wells within the substrate defining the array, and varying a power profile of a motor or other actuator supplying vibration to the substrate.

As used herein, providing or yielding access to tissue includes providing or yielding access to fluid emanating from tissue, such as blood, sweat, wound fluid, and other secretions. The well or receptacle need not directly contact the tissue for tissue access to occur.

Figure 1:
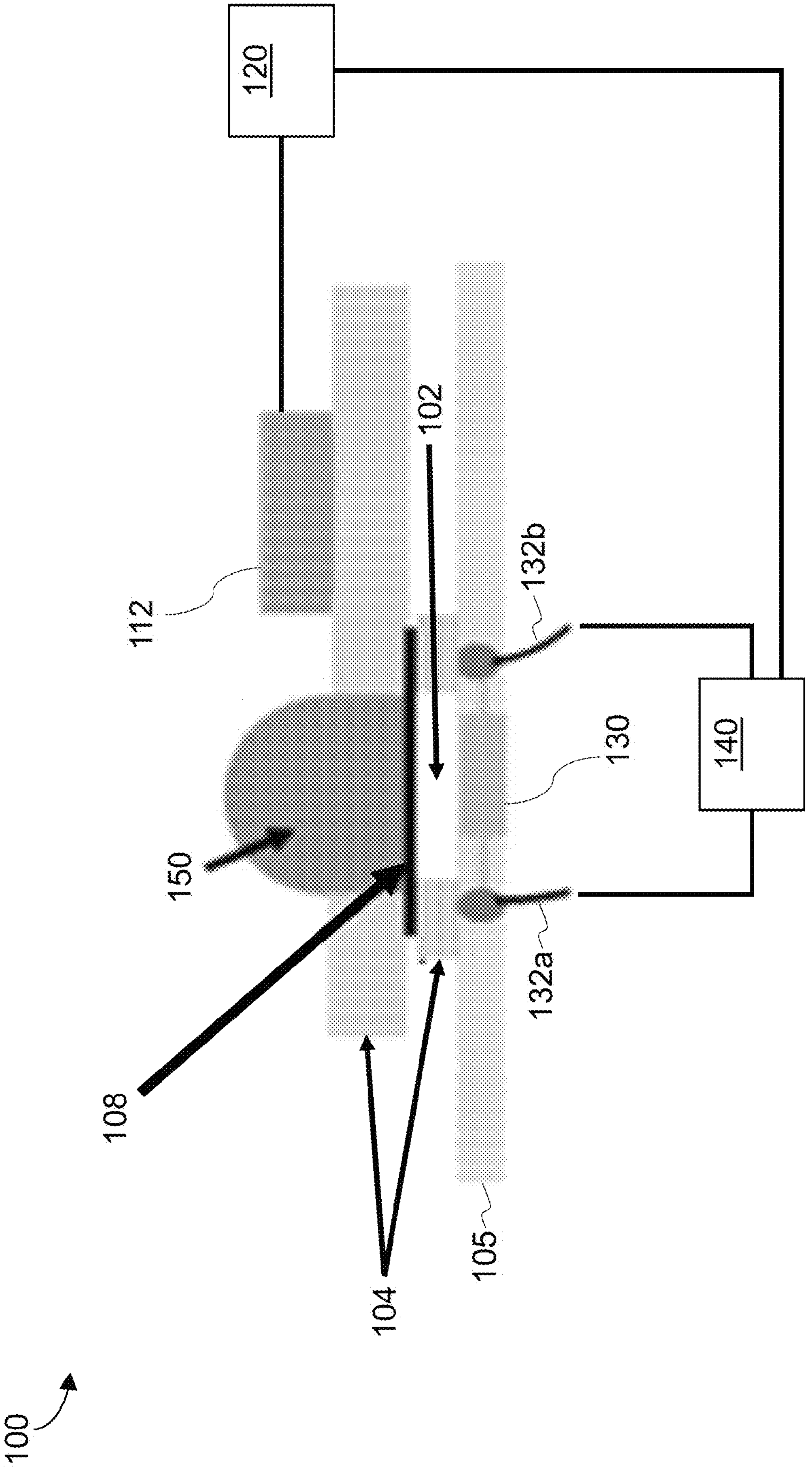
FIG. 1 is a schematic of a cross-section of an example device having a drug delivery and/or sensing component with a selectively-rupturable membrane.

FIG. 1 illustrates an example device 100, shown in cross section. The device 100 includes a well 102 formed by a substrate 104, e.g., a layer of polydimethylsiloxane (PDMS) or other suitable material known to those of skill in the art. A membrane 108, e.g., of one or more layers of graphene oxide (GO) or other suitable known material, is supported by the substrate 104 and disposed at an opening of the well 102. An actuator 112, such as a vibration motor or other suitable known actuator, is configured to supply a vibration to the substrate 104. The actuator 112 is in communication with electronics 120, which are configured to operate the actuator 112. Vibration, as provided by the actuator 112, can cause rupture of the membrane 108, thereby yielding access to a sample 150 (e.g., fluid emanating from a tissue) through the well opening. As illustrated, a sensor 130 is disposed at a base of the well 102 with leads 132*a*, 132*b* extending therefrom. The sensor 130 can be in operative arrangement with a controller 140, e.g., via leads 132*a*, 132*b*, for detection of an analyte present in the sample 150. Optionally, the controller 140 can be in or provide for communication with the electronics 120 that operate the actuator 112. For example, the actuator 112 may be controlled by the controller 140, which can optionally be further connected to the sensor 130 such that control of the actuator 112 is at least partially informed by sensor measurements of the sensor 130.

The substrate 104 can define all or a portion of the well 102. For example, as illustrated in FIG. 1, the substrate 104 forms side walls of the well 102, with the membrane 108 embedded therein, while a base substrate 105 forms a base of the well 102, with the sensor 130 embedded therein. The substrates 104 and 105 can, alternatively, be unitary.

Figure 2:
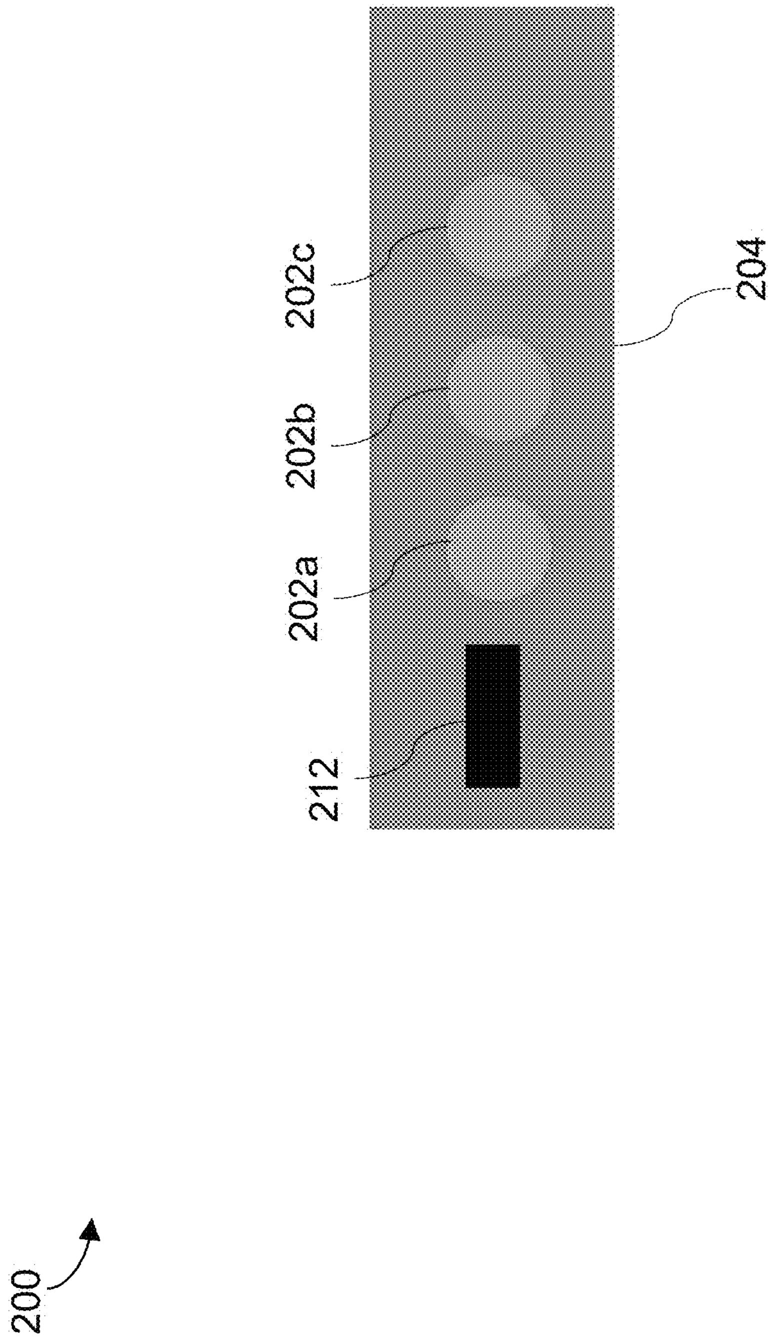
FIG. 2 is a schematic of a top view of an example device with an array of wells.

While a single well is illustrated in cross-section in FIG. 1 for clarity, it should be understood that the substrate can define a plurality of wells. An example of a device 200 having an array of plural wells 202*a-c* formed in a substrate 204 is shown in FIG. 2. As illustrated, the device 200 includes a 1×3 array of wells, with an actuator 212, such as a motor (e.g., a vibration/vibrating motor), disposed at one end of the device 200.

Returning to FIG. 1, a sensor 130 for the detection of an analyte is shown disposed in a well 102. However, the well 102 may alternatively, or in addition, contain a therapeutic substance, such as a drug or ointment. On rupture of the membrane 108, the contents of the well are exposed to the sample 150. Where the sample 150 is, for example, tissue, or a fluid emanating from tissue, any therapeutic substance contained within the well can thereby be delivered to the tissue. Likewise, sensor access to tissue is yielded upon rupture of the membrane.

Figure 3:
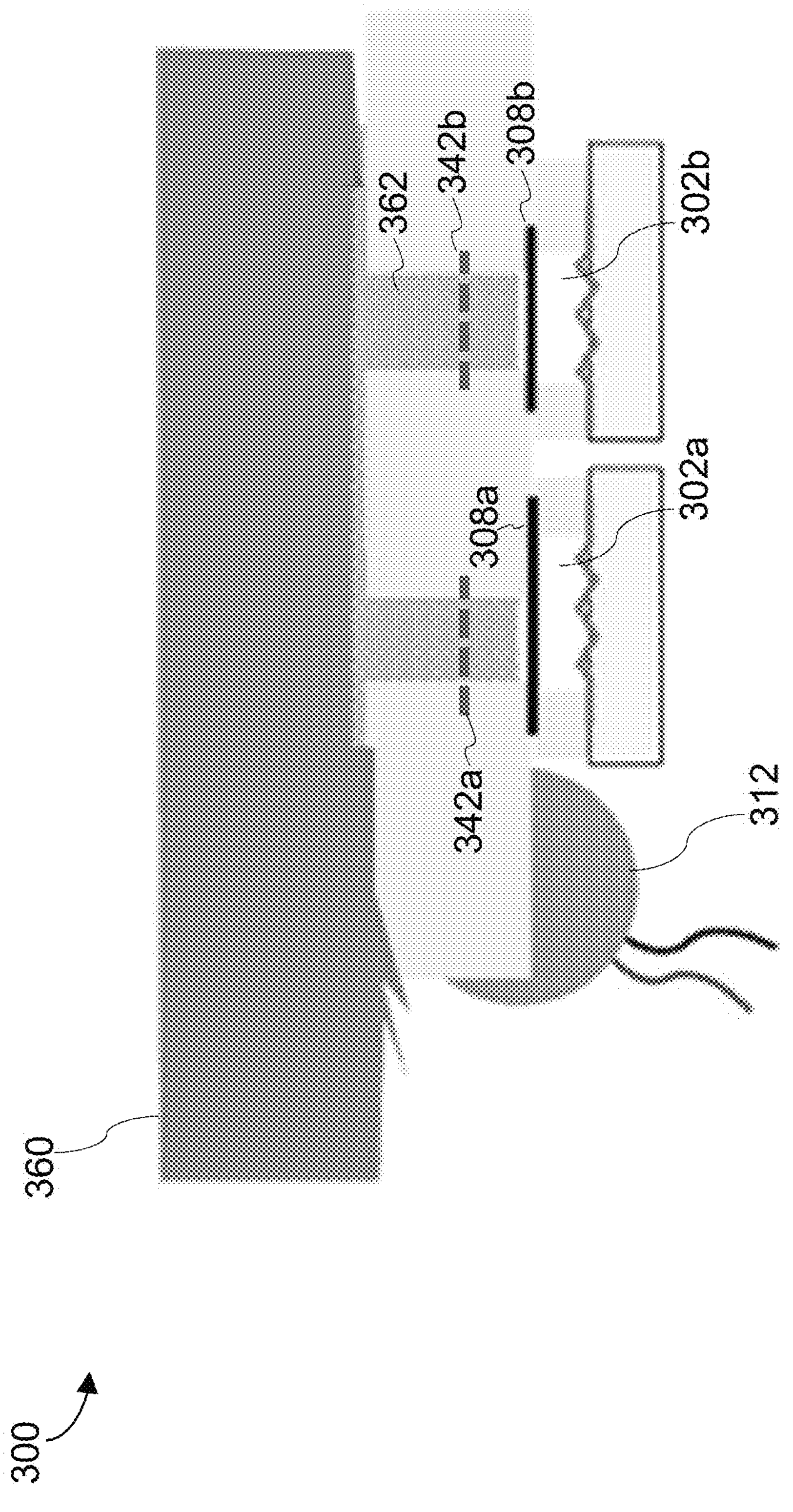
FIG. 3 is a schematic of use of an example device in arrangement with a tissue.

FIG. 3 illustrates an example device 300 in arrangement with a tissue 360. As illustrated, membranes 308*a*, 308*b* provide an interface between wells 302*a*, 302*b* and fluid 362 (e.g., wound fluid from tissue 360). Rupturing the membrane 308*a* at one of the wells 302*a* can thereby break the interface between the wound fluid 362 and an interior portion of that well. An actuator 312 can supply a vibration such that the membrane 308*a* disposed at well 302*a* accumulates a different degree of damage over time than that experienced by the membrane 308*b* disposed at well 302*b*, such that one of the two membranes/wells can be predicted to rupture at a first timepoint and the other of the membranes/wells can be predicted to rupture at a second timepoint.

Optionally, the device 300 may also include porous membranes 342*a* and 342*b*. When covers or membranes, e.g., 308*a* and 308*b*, are fabricated with GO, the GO covers may fracture and loose GO pieces resulting from the fracture may contaminate a wound. Accordingly, porous membranes, e.g., 342*a* and 342*b*, may be placed between GO covers and a wound, for example as shown in FIG. 3, to catch any loose GO pieces resulting from a fracture of the covers.

Figure 4:
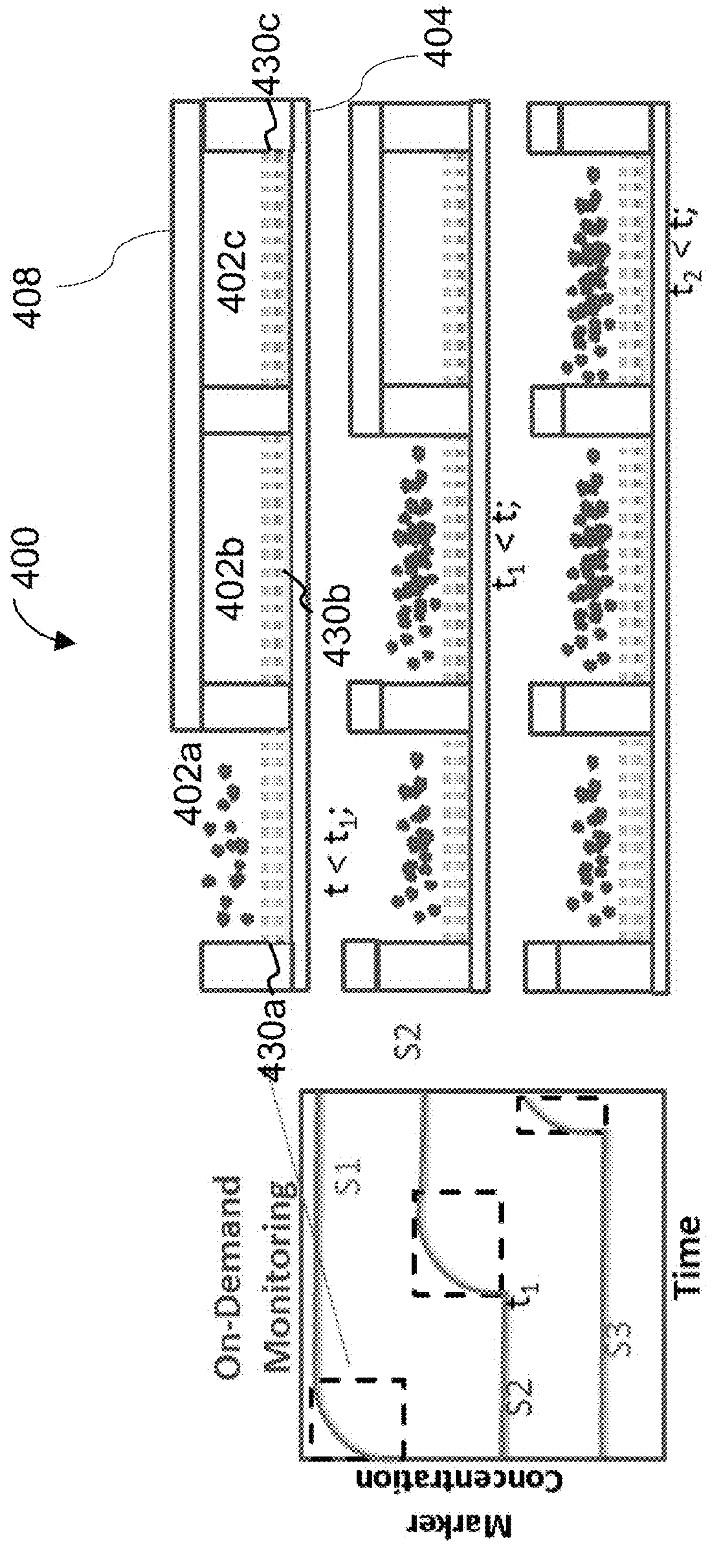
FIG. 4 illustrates on-demand monitoring including a 2D array of cavities or wells.

FIG. 4 illustrates on-demand monitoring including a 2D array of cavities or wells. An array 400 of wells 402*a-c* having respective sensors 430*a-c* is fabricated where all sensors are veiled by a membrane 408. The sensors 430*a-c* are unveiled, for example, sequentially (S1, S2, S3), thereby enabling on-demand removal of the membrane 408 over select wells, e.g., 402*a*, 402*b*, and/or 402*c*, and on-demand monitoring. Each sensor 430*a-c* can be fabricated on a substrate 404.

Removal of Sensor Cover by Acoustic Actuation

Figure 5:
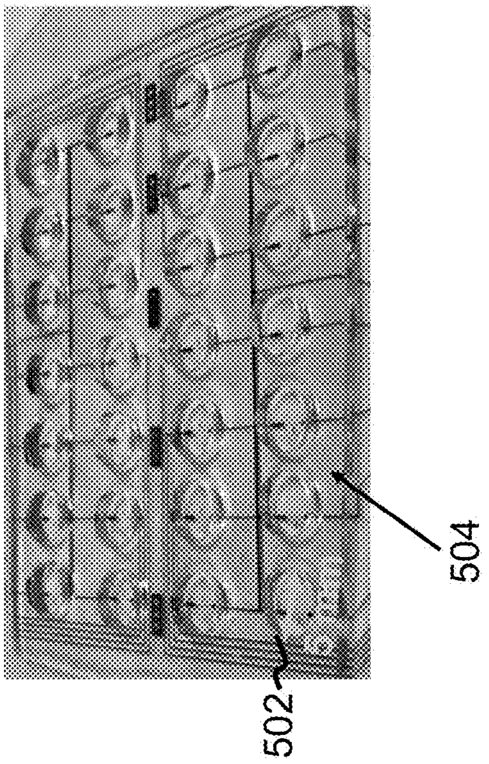
FIG. 5 is an example image of cavities on top of sensor arrays.

FIG. 5 is an example image 500 of cavities on top of sensor arrays. As shown in FIG. 5, a cavity (or well or hole), such as cavity 502, may have a size or width of, e.g., 5 mm. Other cavity sizes/widths are also suitable. To continue, the cavities, e.g., cavity 502, may be formed in a layer or substrate 504 made of material such as PDMS, or any other suitable material known to those of skill in the art. Furthermore, the cavities, e.g., cavity 502, may contain liquid on top of the sensor arrays.

Figure 6:
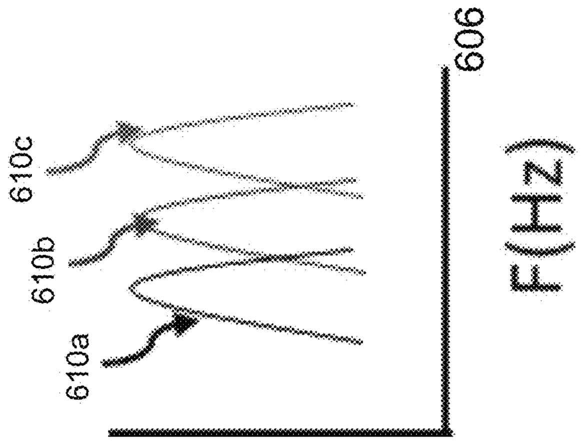
FIG. 6 is an example graph of resonance frequencies.

FIG. 6 is an example graph 600 of resonance frequencies. As shown in FIG. 6, graph 600 indicates frequencies in Hz values 606 and includes example resonance frequencies 610*a*, 610*b*, and 610*c*. The resonance frequencies 610*a*, 610*b*, and 610*c* may be used to perform acoustic actuation, which may also be referred to as vibration actuation. As part of performing acoustic actuation, a resonance frequency, e.g., 610*a*, 610*b*, or 610*c*, may be matched with a corresponding membrane size, e.g., a size for membrane 108 (FIG. 1) or 308*a*-308*b* (FIG. 3).

FIGS. 7A, 7B, 7C, 7D, 7E, and 7F illustrate respective examples 700*a*, 700*b*, 700*c*, 700*d*, 700*e*, and 700*f* of acoustic actuation for different cavity sizes. As shown in example 700*a* of FIG. 7A, a substrate 704*a* (e.g., a layer of PDMS or other suitable known material) may include a cavity/hole 702*a*. The cavity 702*a* may initially be covered on top by a membrane 708*a*, which may be, e.g., an elastomeric thin film. Other membrane materials and/or thicknesses are also suitable. To continue, cavity 702*a* may have a size of, e.g., 4 mm, which size may correspond to resonant frequency 710*a*. Further, membrane 708*a* may include a small preformed crack or notch 714*a*, which may be configured to propagate during acoustic actuation. It is noted that, instead of a crack or notch, another suitable known geometry or configuration that acts as a stress concentrator, such as a hole, groove, or fillet, among other examples, may also be used. As shown in example 700*b* of FIG. 7B, when an acoustic wave is generated at resonant frequency 710*a* corresponding to the size of membrane 708*a*, this may lead to vibration in membrane 708*a* and eventual delamination at propagated crack site 714*a* of FIG. 7A.

Figure 7B:
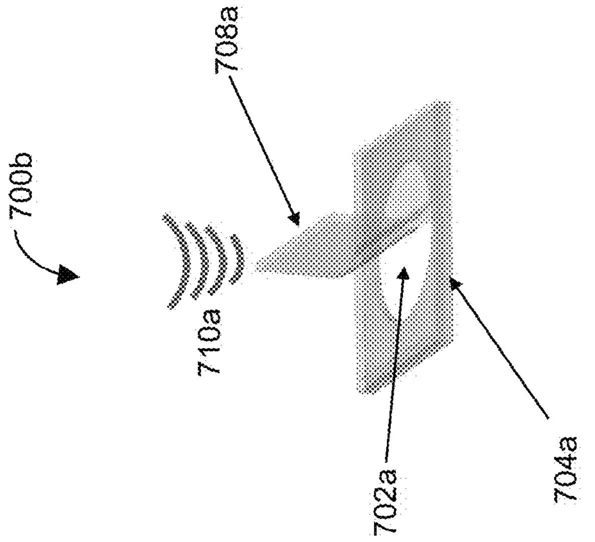
FIGS. 7A-F illustrate examples of acoustic actuation for different cavity sizes.
Figure 7A:
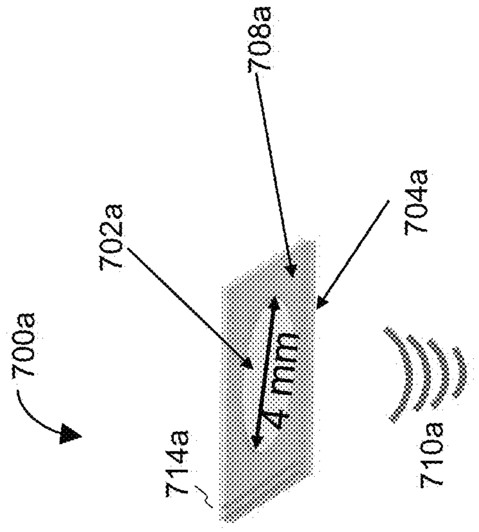
Figure 7D:
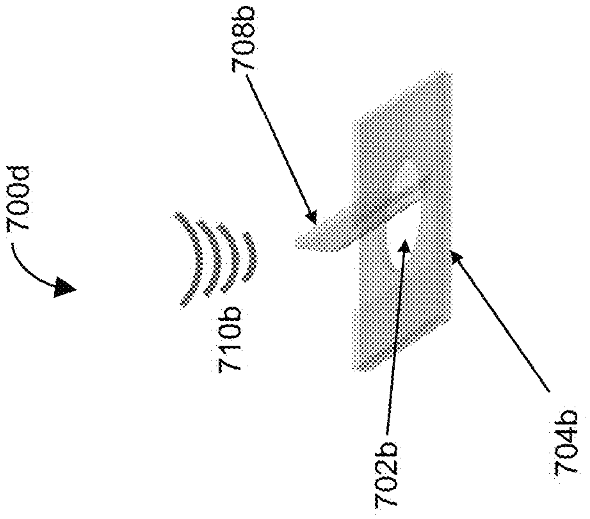
Figure 7C:
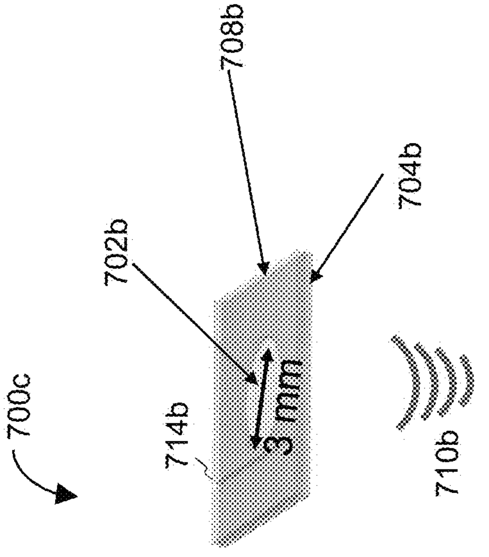
Figure 7F:
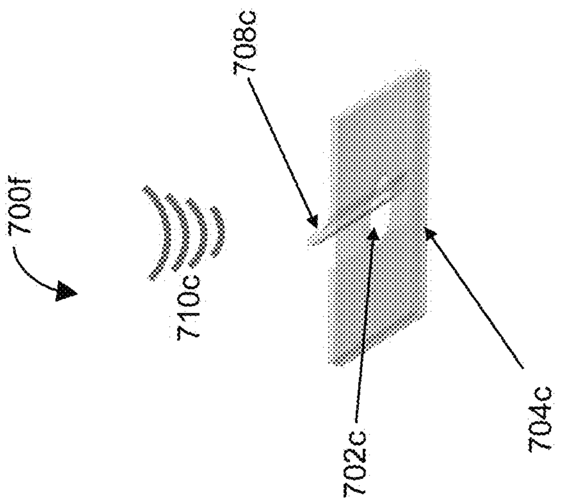

Moreover, as shown in example 700*c* of FIG. 7C, a substrate 704*b* (e.g., a layer of PDMS or other suitable known material) may include a cavity/hole 702*b*. The cavity 702*b* may initially be covered on top by a membrane 708*b*, which may be, e.g., an elastomeric thin film. Other membrane materials and/or thicknesses are also suitable. To continue, cavity 702*b* may have a size of, e.g., 3 mm, which size may correspond to resonant frequency 710*b*. Further, membrane 708*b* may include a small preformed crack or notch 714*b*, which may be configured to propagate during acoustic actuation. As shown in example 700*d* of FIG. 7D, when an acoustic wave is generated at resonant frequency 710*b* corresponding to the size of membrane 708*b*, this may lead to vibration in membrane 708*b* and eventual delamination at propagated crack site 714*b* of FIG. 7C.

Figure 7E:
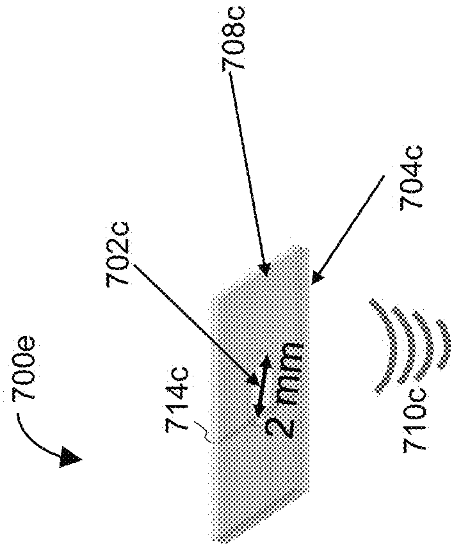

Finally, as shown in example 700*e* of FIG. 7E, a substrate 704*c* (e.g., a layer of PDMS or other suitable known material) may include a cavity/hole 702*c*. The cavity 702*c* may initially be covered on top by a membrane 708*c*, which may be, e.g., an elastomeric thin film. Other membrane materials and/or thicknesses are also suitable. To continue, cavity 702*c* may have a size of, e.g., 2 mm, which size may correspond to resonant frequency 710*c*. Further, membrane 708*c* may include a small preformed crack or notch 714*c*, which may be configured to propagate during acoustic actuation. As shown in example 700*f* of FIG. 7F, when an acoustic wave is generated at resonant frequency 710*f* corresponding to the size of membrane 708*f*, this may lead to vibration in membrane 708*c* and eventual delamination at propagated crack site 714*c* of FIG. 7E.

Thus, as shown by FIGS. 7A-7E described hereinabove, by changing a frequency of an acoustic wave, e.g., frequency 714*a* (FIG. 7A), 714*b* (FIG. 7C), or 714*c* (FIG. 7E), different cavities, e.g., cavity 702*a* (FIG. 7A), 702*b* (FIG. 7C), or 702*c* (FIG. 7E), may selectively open, giving access to only a certain set of sensors.

Graphene Oxide Covers

Figure 8:
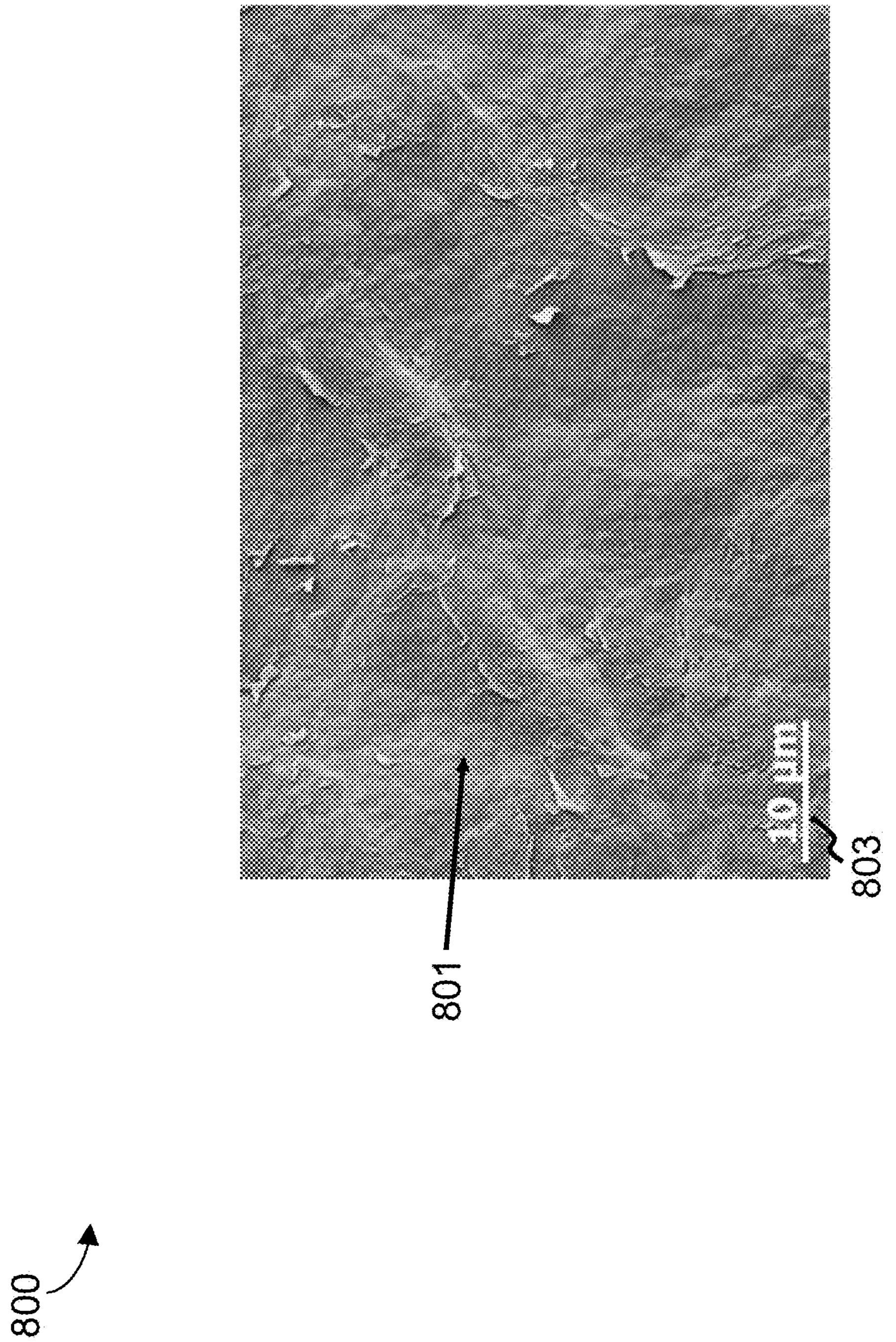
FIG. 8 is an example magnified image of a portion of graphene oxide.

FIG. 8 is an example magnified image 800 of a portion 801 of graphene oxide. As shown in FIG. 8, image 800 may display portion 801 at a scale 803 of 10 μm. The portion 801 may be a portion of a membrane, e.g., membrane 108 (FIG. 1), 308*a*-308*b* (FIG. 3), or 708*a*-708*c* (FIGS. 7A-7E).

Figure 9:
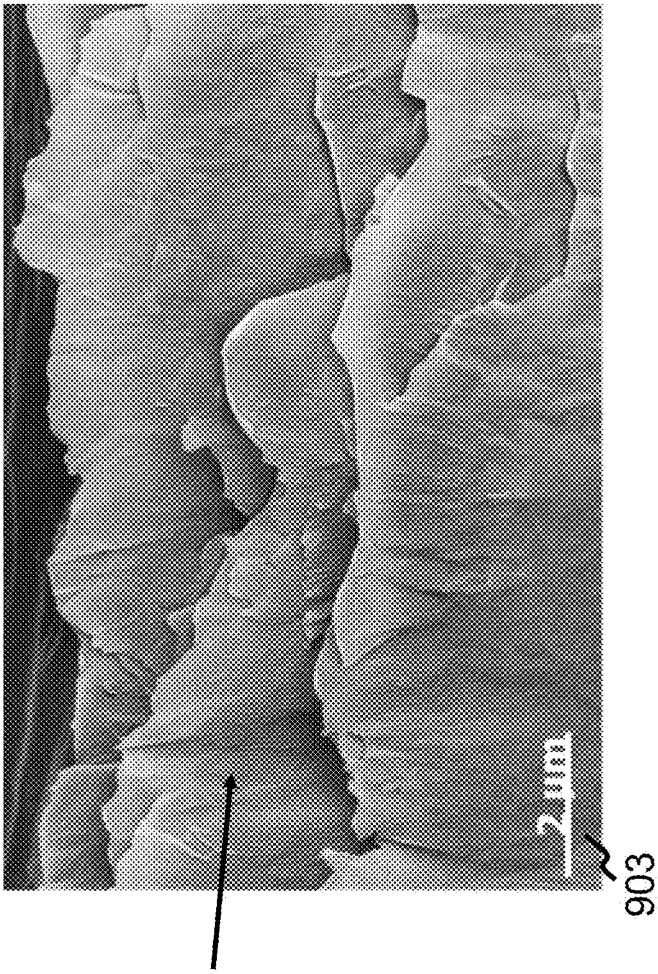
FIG. 9 is another example magnified image of a portion of graphene oxide.

FIG. 9 is another example magnified image 900 of a portion 901 of graphene oxide. As shown in FIG. 9, image 900 may display portion 901 at a scale 903 of 2 μm. The portion 901 may be a portion of a membrane, e.g., membrane 108 (FIG. 1), 308*a*-308*b* (FIG. 3), or 708*a*-708*c* (FIGS. 7A-7E).

Devices and methods of the present disclosure may use graphene oxide as a material for a membrane, e.g., membrane 108 (FIG. 1), 308*a*-308*b* (FIG. 3), or 708*a*-708*c* (FIGS. 7A-7E). However, embodiments are not limited to graphene oxide, and any other suitable material known to those of skill in the art may also be used.

Single Well

Figure 10:
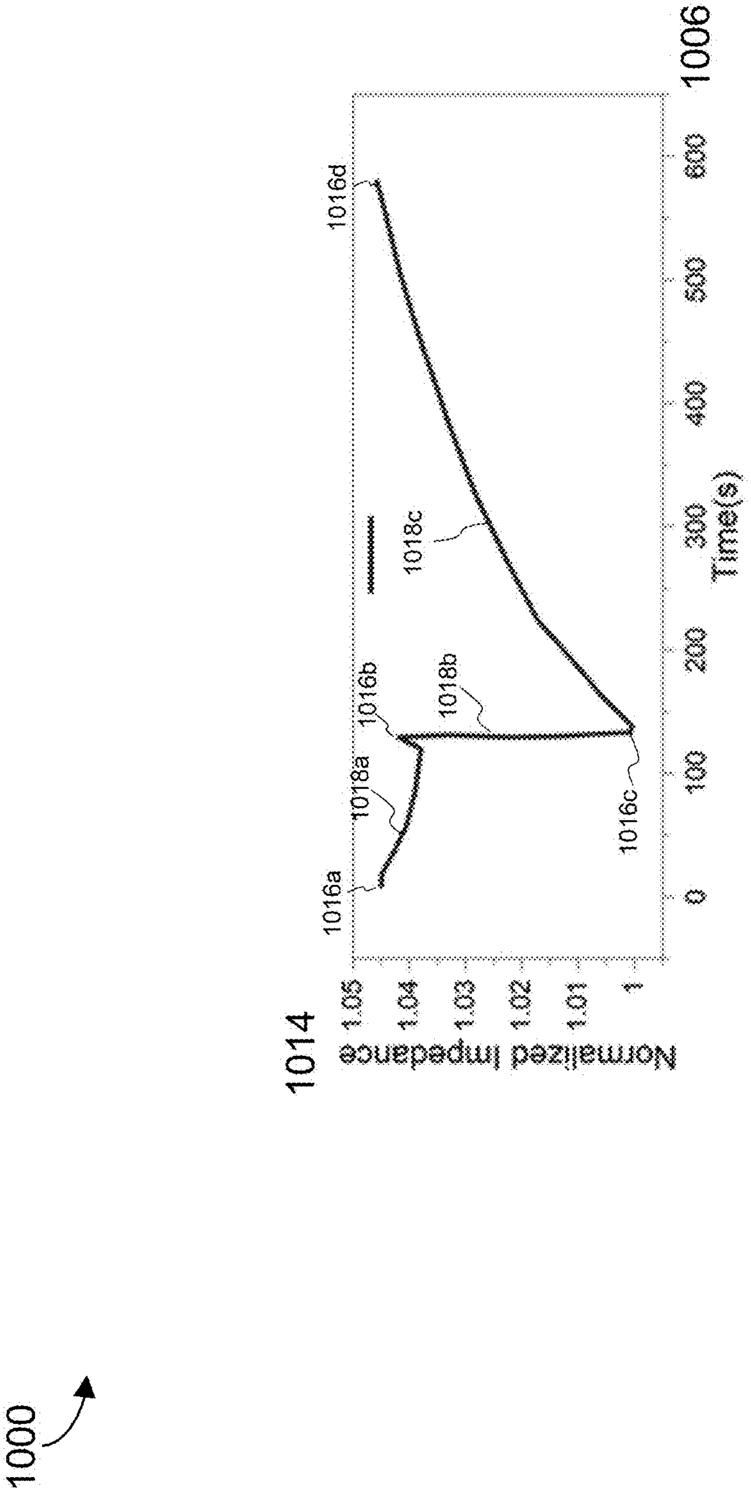
FIGS. 10-12 are example graphs of results of using an actuator to open a cover or membrane.
Figure 11:
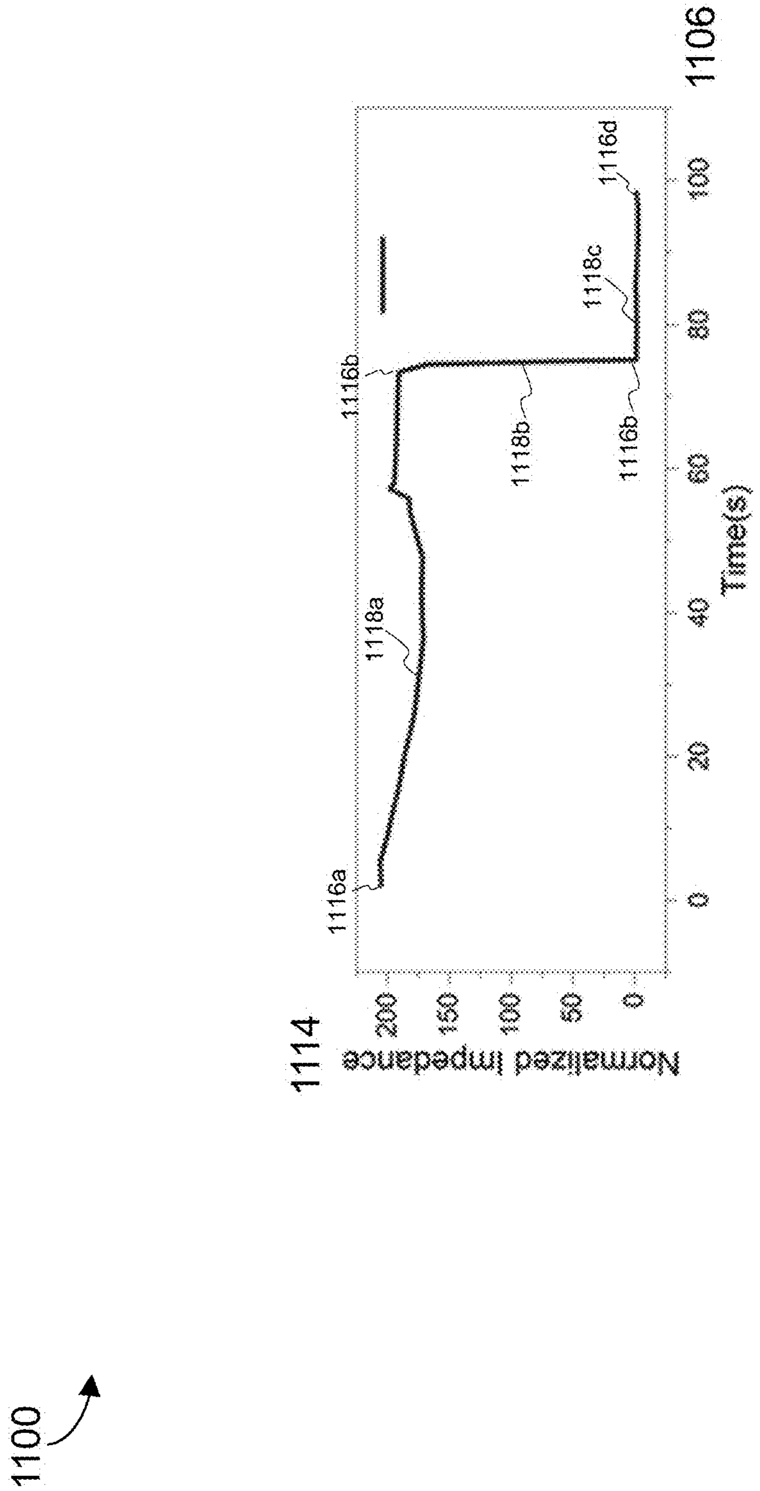
Figure 12:
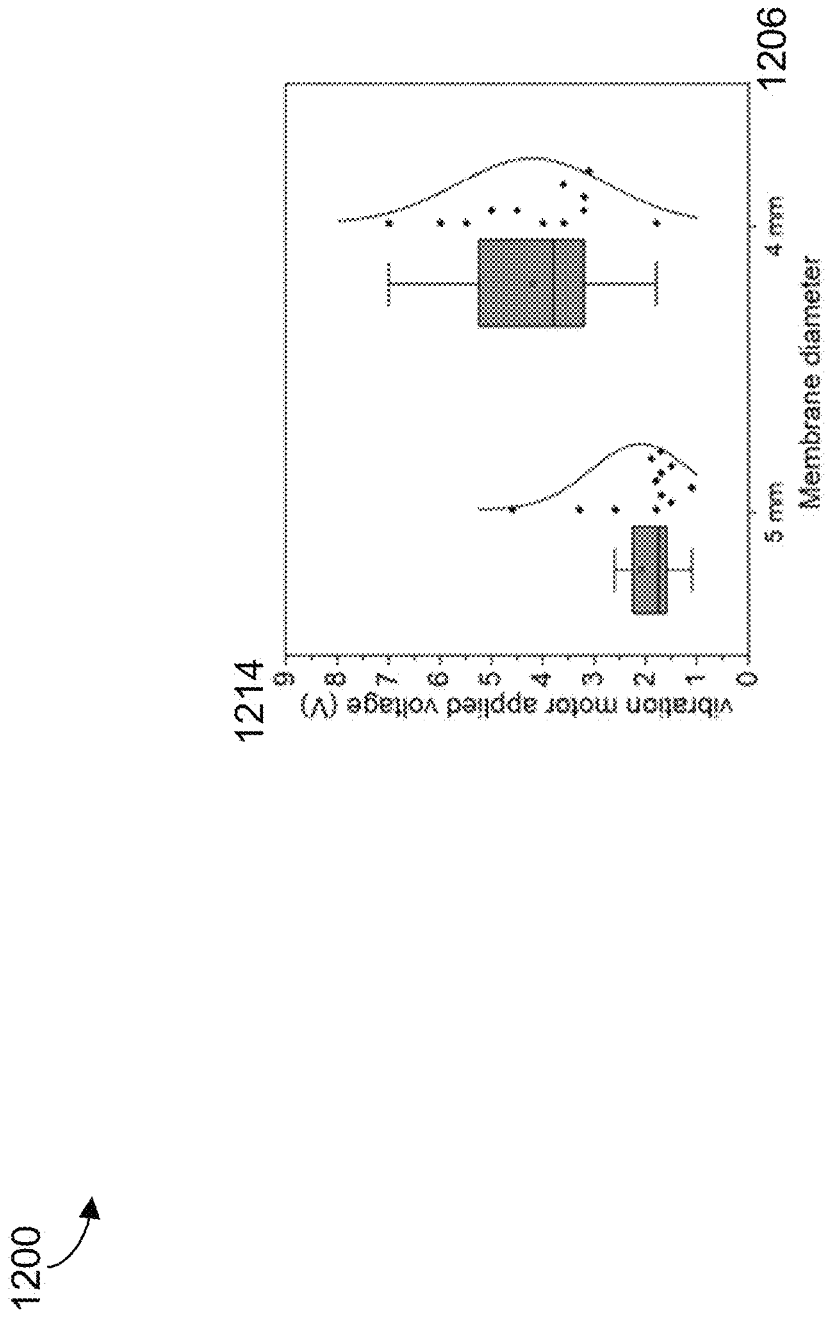

FIGS. 10, 11, and 12 are example graphs 1000, 1100, and 1200, respectively, of results using an actuator, e.g., 112 (FIG. 1), 212 (FIG. 2), or 312 (FIG. 3), such as a vibration/vibrating motor or other suitable known actuator, to open a cover or membrane, e.g., 108 (FIG. 1), 308*a-b* (FIG. 3), or 708*a-c* (FIGS. 7A-7E), such as a GO membrane or membrane fabricated from another suitable known material.

FIG. 10 is an example graph 1000 of normalized impedance 1014 over time 1006. The example graph 1000 may chart normalized impedance 1014 as it changes over time 1006 depending on a condition of a single cavity or well, e.g., well 102 (FIG. 1), 202*a-c* (FIG. 2), 302*a-b* (FIG. 3), or 702*a-c* (FIGS. 7A-7E). The well's condition prior to breaking or opening a membrane cover of the well may be different compared to the well's condition while the membrane is being opened, which again may be different compared to the well's condition after the membrane is opened. As shown in FIG. 10, an initial condition of the single well may be indicated by region 1018*a* between points 1016*a* and 1016*b* in graph 1000. The region 1018*a* may reflect that the well initially contains a buffer solution, such as PBS (phosphate-buffered saline). However, any suitable liquid or solution known in the art may be used; further, a well may instead initially contain, e.g., air or another suitable known gas or mixture of gases. To continue, region 1018*b* between points 1016*b* and 1016*c* in graph 1000 may indicate the single well's condition while the membrane cover is being opened. Finally, region 1018*c* between points 1016*c* and 1016*d* in graph 1000 may indicate the well's condition after the membrane cover is opened—when, for example, wound fluid begins to enter the well.

FIG. 11 is an example graph 1100 of normalized impedance 1114 over time 1106. The example graph 1100 may chart normalized impedance 1114 as it changes over time 1106 depending on a condition of a single cavity or well, e.g., well 102 (FIG. 1), 202*a-c* (FIG. 2), 302*a-b* (FIG. 3), or 702*a-c* (FIGS. 7A-7E). The well's condition prior to breaking or opening a membrane cover of the well may be different compared to the well's condition while the membrane is being opened, which again may be different compared to the well's condition after the membrane is opened. As shown in FIG. 11, an initial condition of the single well may be indicated by region 1118*a* between points 1116*a* and 1116*b* in graph 1100. The region 1118*a* may reflect that the well initially contains a gas, e.g., air. However, any suitable gas or mixture of gases known in the art may be used; further, a well may instead initially contain, e.g., PBS or another suitable known buffer or solution. To continue, region 1118*b* between points 1116*b* and 1116*c* in graph 1100 may indicate the single well's condition while the membrane cover is being opened. Finally, region 1118*c* between points 1116*c* and 1116*d* in graph 1100 may indicate the well's condition after the membrane cover is opened—when, for example, PBS begins to enter the well.

FIG. 12 is an example graph 1200 of vibration motor applied voltage 1214 relative to membrane diameter 1206. As shown in FIG. 12, graph 1200 may be a box plot depicting vibration motor applied voltage 1214 relative to membrane diameter 1206 for membrane diameters of, e.g., 5 mm and 4 mm. Other membrane diameters are also suitable.

Extension to Multiple Wells

Figure 13:
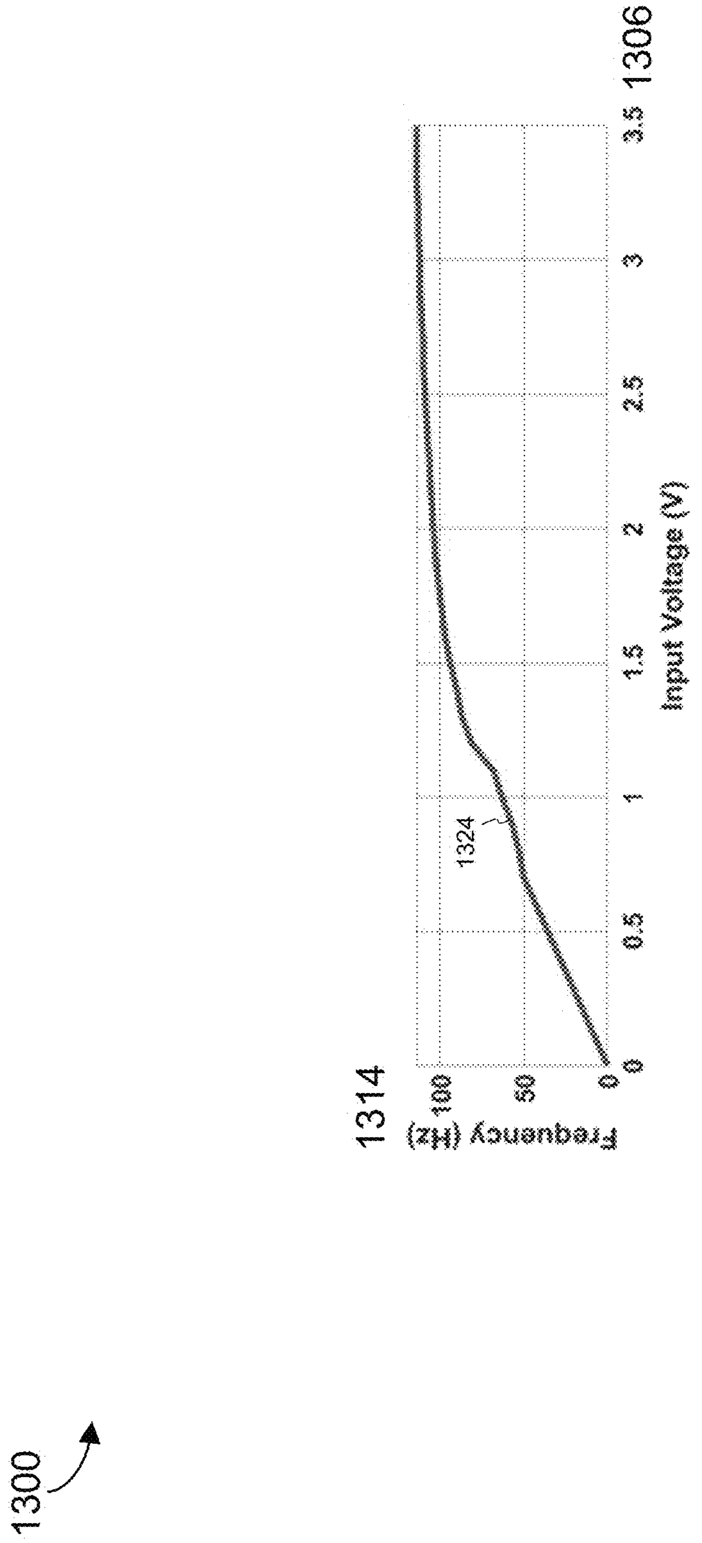
FIGS. 13-14 are example graphs of results of using an actuator to open covers or membranes for a device having multiple wells or cavities.
Figure 14:
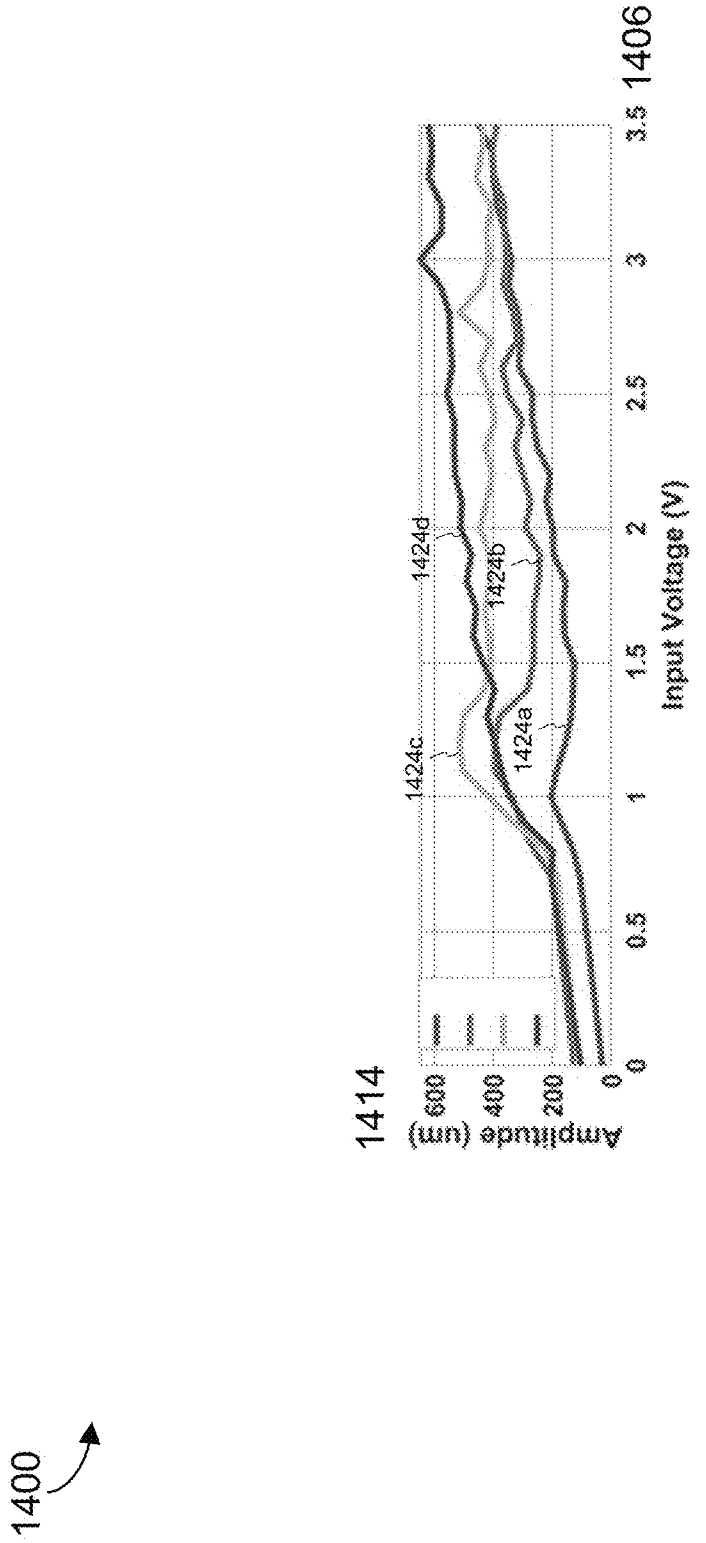

FIGS. 13 and 14 are example graphs 1300 and 1400, respectively, of results using an actuator, e.g., 112 (FIG. 1), 212 (FIG. 2), or 312 (FIG. 3), such as a vibration/vibrating motor or other suitable known actuator, to open a covers or membranes for a device having multiple wells or cavities, e.g., device 200 having wells 202*a-c* (FIG. 2) or device 300 having wells 302*a-b* (FIG. 3).

FIG. 13 is an example graph 1300 of frequency 1314 relative to input voltage 1306. The input voltage 1306 may be voltage input to an actuator or motor (the latter such as a vibration/vibrating motor), e.g., motor 112 (FIG. 1), 212 (FIG. 2), or 312 (FIG. 3). As shown by line 1324 of FIG. 13, frequency 1314 generated by the actuator may increase as input voltage 1306 increases.

FIG. 14 is an example graph 1400 of amplitude 1414 relative to input voltage 1406. The input voltage 1406 may be voltage input to an actuator or motor (the latter such as a vibration/vibrating motor), e.g., actuator 112 (FIG. 1), 212 (FIG. 2), or 312 (FIG. 3). As shown by lines 1424*a-d* of FIG. 14, amplitude 1414 generated by the actuator may trend upward as input voltage 1406 increases. The lines 1424*a*, 1424*b*, 1424*c*, and 1424*d* may indicate amplitude of vibration, in, e.g., μm, for a substrate (e.g., 204 of FIG. 2), a first well (e.g., 202*a* of FIG. 2), a second well (e.g., 202*b* of FIG. 2), and a third well (e.g., 202*c* of FIG. 2), respectively.

Systematic Approach

Figure 15:
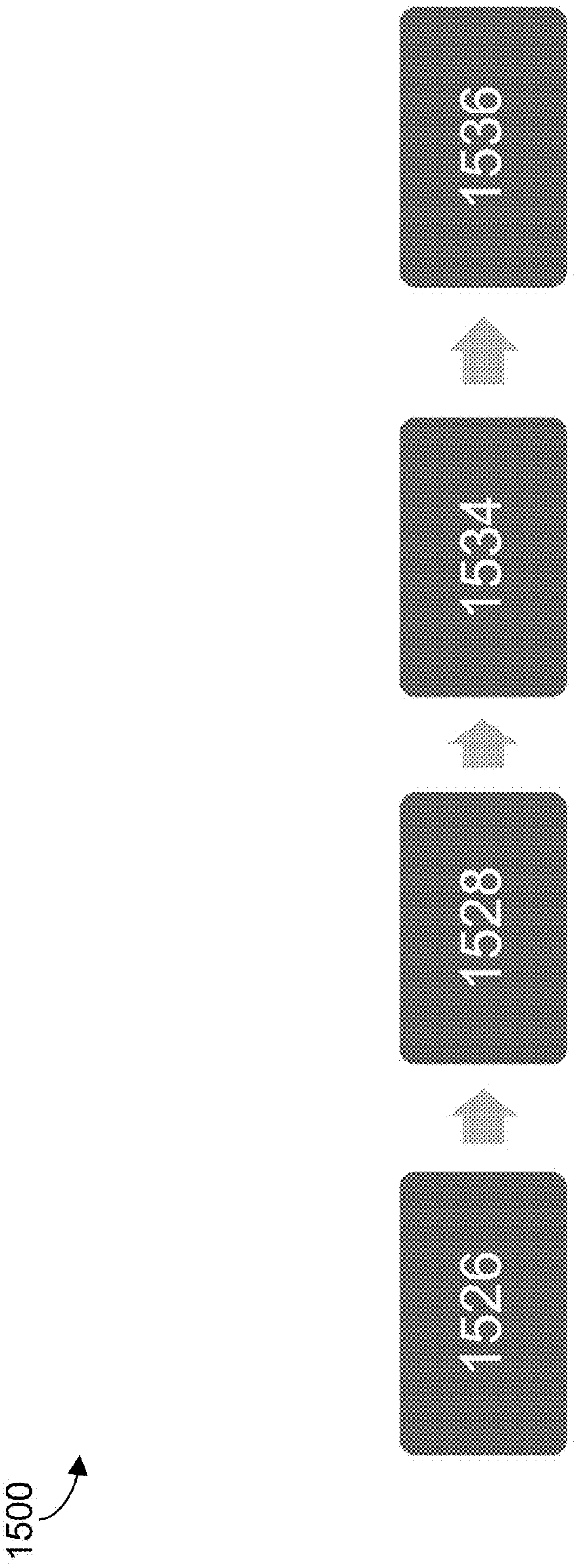
FIG. 15 is an example process for a systematic approach to vibration-based rupture of membranes for sensing and drug release.

FIG. 15 is an example process 1500 of a systematic approach to vibration-based rupture of membranes for sensing and drug release. As shown in FIG. 15, example process 1500 includes four stages: 1526, 1528, 1534, and 1536. The stage 1526 may include excitation, geometry, and material properties; the stage 1528 may include frequency-dependent structural modeling; the stage 1534 may include amplitude of vibration at membrane covers; and the stage 1536 may include damage accumulation to predict breaking.

Excitation, Geometry, and Material Properties

As part of stage 1526 of example process 1500, excitation may include frequency, amplitude, direction, and location of applied vibration, e.g., vibration applied by actuator 112 (FIG. 1), 212 (FIG. 2), or 312 (FIG. 3). Likewise, geometry may include diameter, thickness, and added mass of membranes, e.g., membranes 108 (FIG. 1), 308*a*-308*b* (FIG. 3), and/or 708*a*-708*c* (FIGS. 7A-7E), as well as geometry of a vibrating device, e.g., device 100 (FIG. 1), 200 (FIG. 2), or 300 (FIG. 3). And material properties (i.e., of membranes) may include elastic modulus and density.

Frequency-Dependent Structural Modeling

Figure 16A:
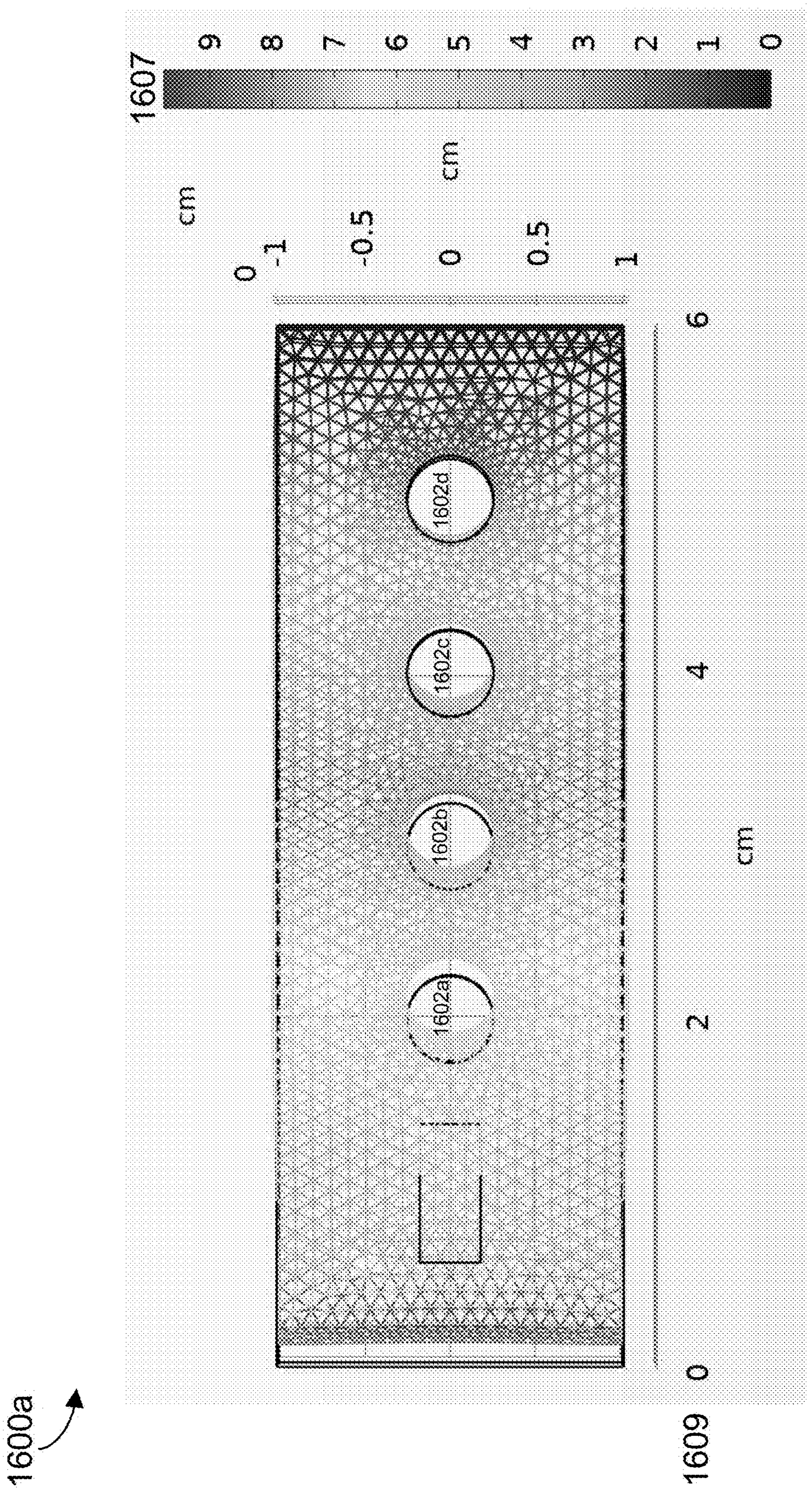
FIGS. 16A-B are example color-coded images of acceleration of vibration of a device.
Figure 16B:
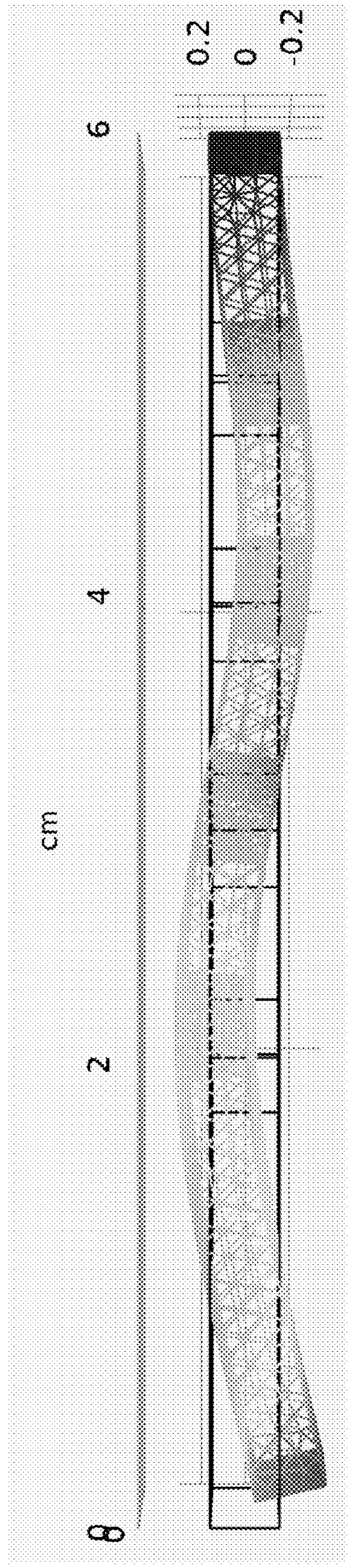

FIGS. 16A and 16B are example color-coded images 1600*a* and 1600*b*, respectively, of acceleration of vibration of a device, e.g., device 100 (FIG. 1), 200 (FIG. 2), or 300 (FIG. 3). As shown in FIG. 16A, a color scale 1607 may indicate acceleration in m/s 2 when a given frequency, e.g., 75 Hz, is applied. Other frequency values are also suitable. To continue, image 1600*a* may depict a horizontal location 1609 of four wells or cavities 1602*a-d*. For example, well 1602*a* may be at 2 cm, well 1602*b* may be at 3 cm, well 1602*c* may be at 4 cm, and well 1602*d* may be at 5 cm. Other horizontal location values are also suitable.

Figure 17:
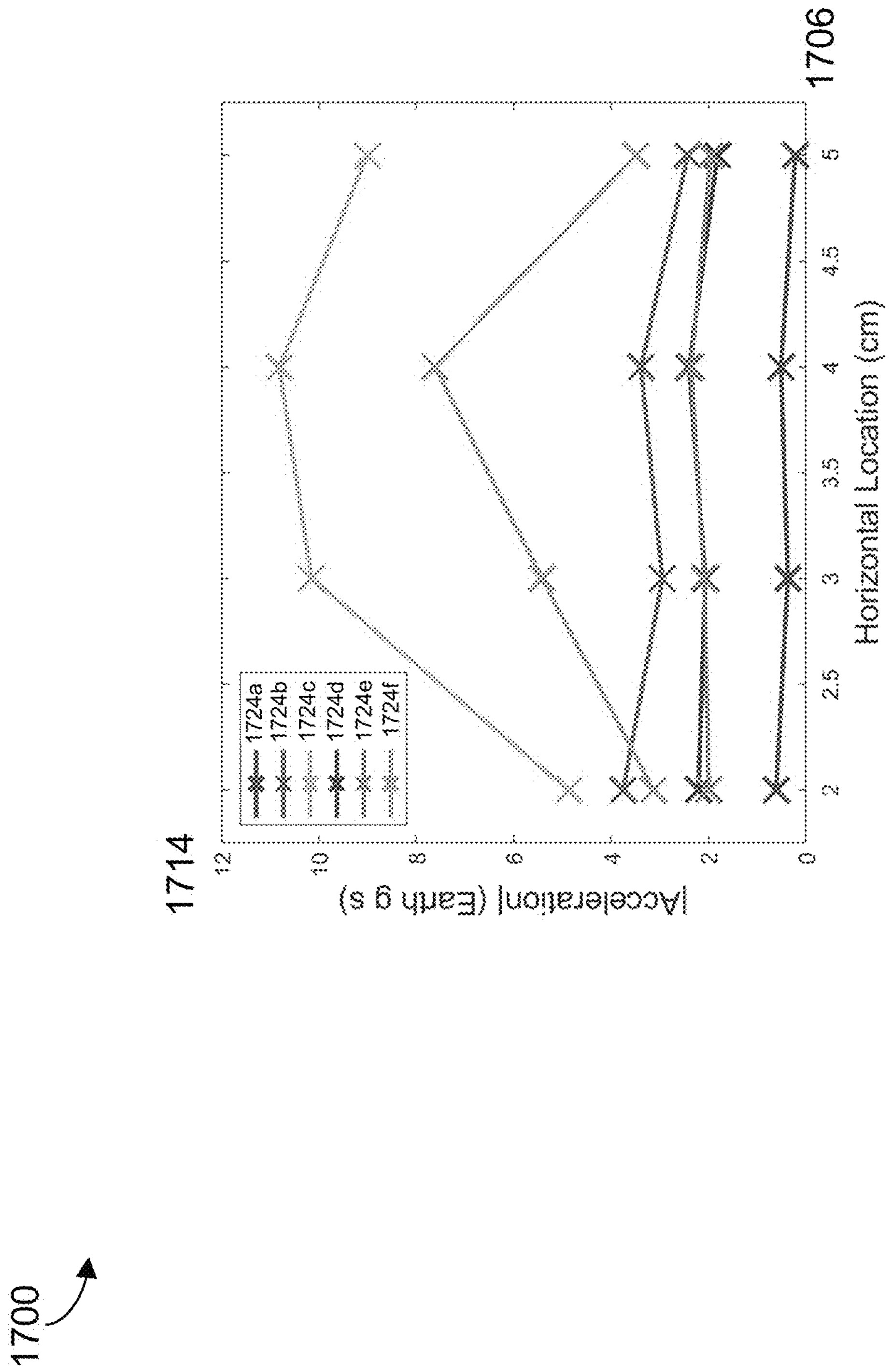
FIG. 17 is an example graph of absolute acceleration based on horizontal location.

FIG. 17 is an example graph 1700 of absolute acceleration 1714 based on horizontal location 1706. The graph 1700 may depict simulated results for average acceleration 1714 in, for example, Earth g values, depending on horizontal location 1706 of a well, e.g., well 1602*a*, 1602*b*, 1602*c*, or 1602*d* (FIG. 16A), in for instance, cm. As shown in FIG. 17, the graph 1700 may depict absolute acceleration 1714 based on horizontal location 1706 at various frequencies, e.g., frequencies 1724*a*, 1724*b*, 1724*c*, 1724*d*, 1724*e*, and 1724*f*, which may correspond to, e.g., 75 Hz, 100 Hz, 125 Hz, 150 Hz, 175 Hz, and 200 Hz, respectively. Other frequency values are also suitable. To continue, a simulated resonance for a 115 Hz frequency (not shown) may have a peak acceleration exceeding 35 Earth g values. The simulated results depicted in FIG. 17 may reflect a proportional increase in applied amplitude with frequency.

It is also noted that FIGS. 16A-B and 17 may depict example simulated results at stage 1528 of example process 1500 (FIG. 15).

Amplitude of Vibration at Membrane Covers

Figure 18:
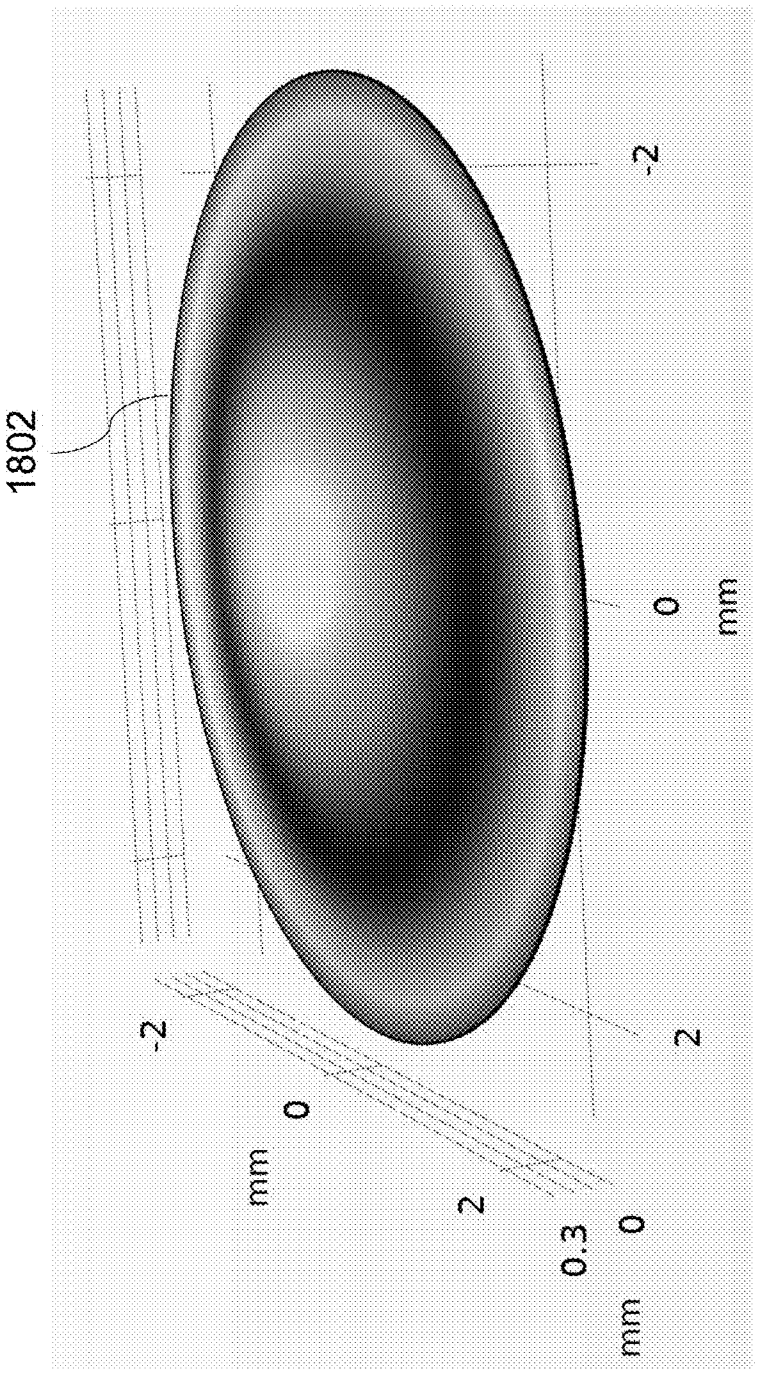
FIG. 18 is an example color-coded image of amplitude of vibration for a membrane.

FIG. 18 is an example color-coded image 1800 of amplitude of vibration for a membrane 1802. The membrane 1802 may have a diameter of, e.g., 5 mm. Other diameter values are also suitable.

Figure 19:
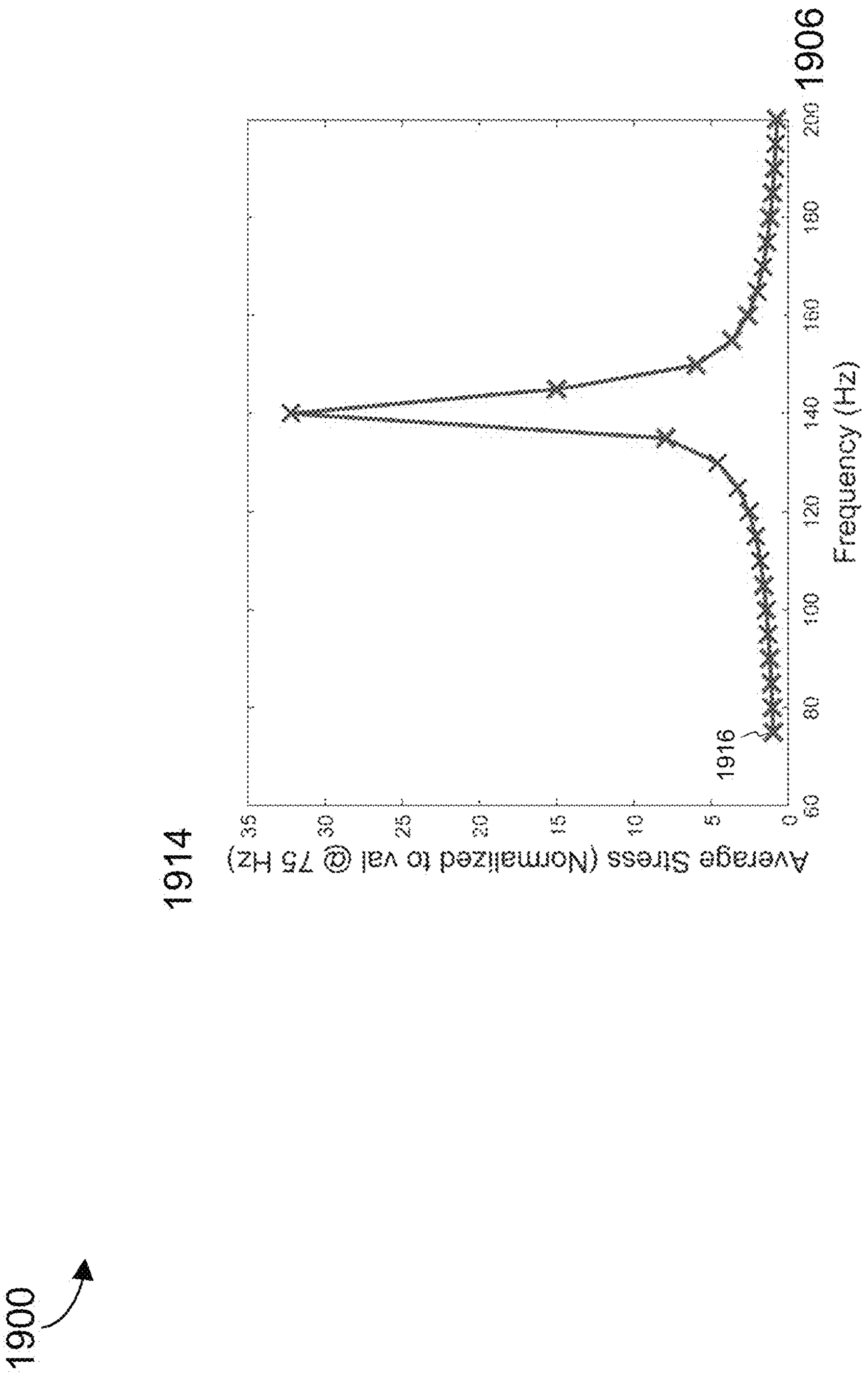
FIG. 19 is an example graph of average stress based on frequency.

FIG. 19 is an example graph 1900 of average stress 1914 based on frequency 1906. The graph 1900 may depict simulated results for average stress 1914 depending on frequency 1906, in for example, Hz, applied to a membrane, e.g., membrane 1802 (FIG. 18) with a diameter of 5 mm. Furthermore, the membrane 1802 may have an elastic modulus of 5 GPa and 30 mg of added mass. Other elastic modulus and/or added mass values are also suitable. To continue, average stress 1914 may be normalized to a value at frequency 1906 of 75 Hz, e.g., a value at point 1916 of graph 1900. Further, a uniform body load (N/m 3) may be applied across frequencies shown in graph 1900. Results depicted in graph 1900 may indicate that average stress and maximum stress are similar in a simulation.

Figure 20:
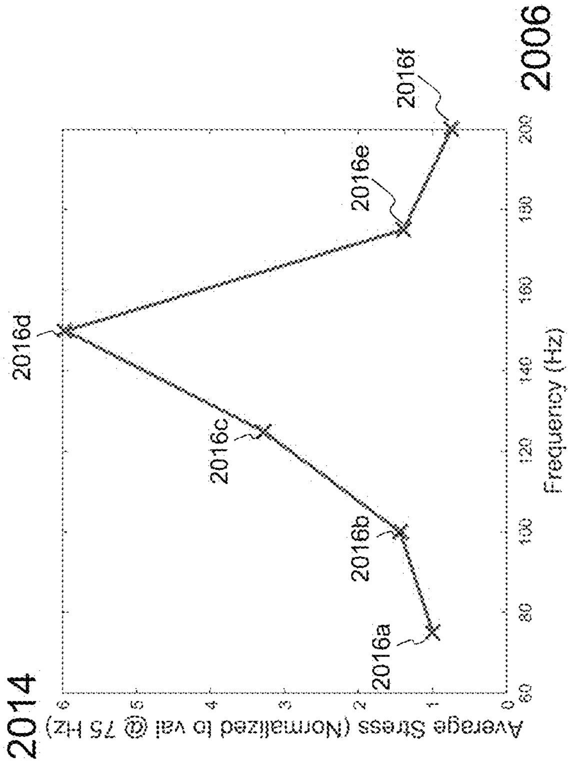
FIG. 20 is another example graph of average stress based on frequency.

FIG. 20 is another example graph 2000 of average stress 2014 based on frequency 2006. The graph 2000 may depict simulated results for average stress 2014 depending on frequency 2006, in for example, Hz, applied to a membrane, e.g., membrane 1802 (FIG. 18) with a diameter of 5 mm. Further, graph 2000 may include points 2016*a*, 2016*b*, 2016*c*, 2016*d*, 2016*e*, and 2016*f* that correspond to frequency values 1724*a* (e.g., 75 Hz), 1724*b* (e.g., 100 Hz), 1724*c* (e.g., 125 Hz), 1724*d* (e.g., 150 Hz), 1724*e* (e.g., 175 Hz), and 1724*f* (e.g., 200 Hz) (FIG. 17), respectively.

Figure 21:
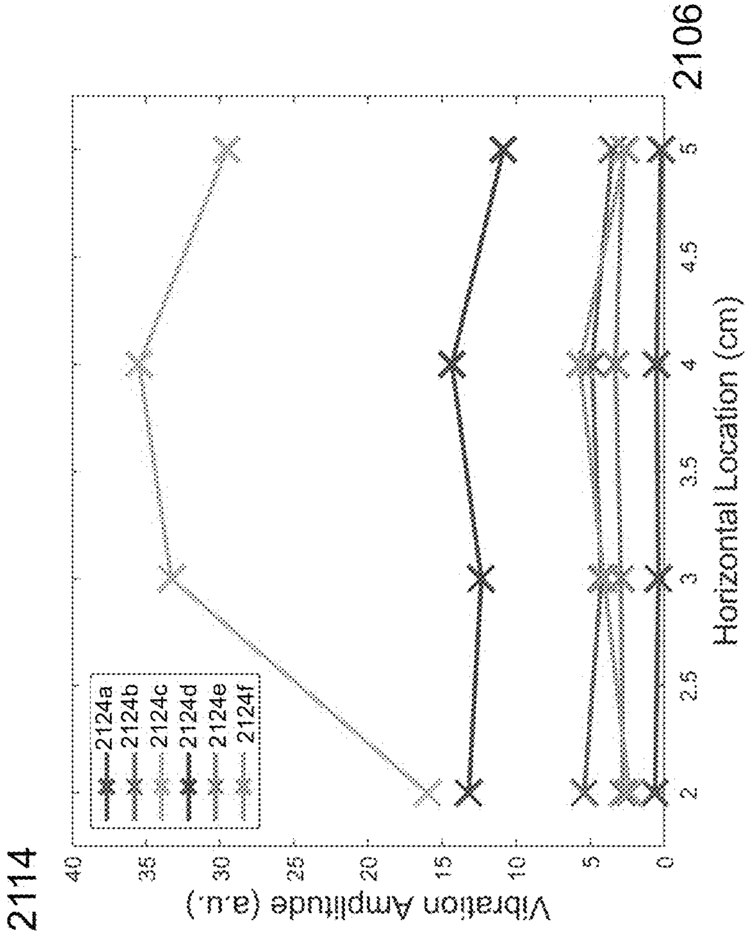
FIG. 21 is an example graph of vibration amplitude based on horizontal location.

FIG. 21 is an example graph 2100 of vibration amplitude 2114 based on horizontal location 2106. The graph 2100 may depict simulated results for vibration amplitude 2114 in, for example, arbitrary units, depending on horizontal location 2106 of a well, e.g., well 1602*a*, 1602*b*, 1602*c*, or 1602*d* (FIG. 16), in for instance, cm. As shown in FIG. 21, the graph 2100 may depict vibration amplitude 2114 based on horizontal location 2106 at various frequencies, e.g., frequencies 2124*a*, 2124*b*, 2124*c*, 2124*d*, 2124*e*, and 2124*f*, which may correspond to, e.g., 75 Hz, 100 Hz, 125 Hz, 150 Hz, 175 Hz, and 200 Hz, respectively. Other frequency values are also suitable. To continue, values displayed in graph 2100 may be arrived at by multiplying absolute acceleration 1714 values from graph 1700 (FIG. 17) by corresponding average stress 2014 values from graph 2000 (FIG. 20) for each horizontal location 2106. The graph 2100 of FIG. 21 may also reflect simulated intensity of vibration according to frequency, e.g., frequencies 2124*a*, 2124*b*, 2124*c*, 2124*d*, 2124*e*, or 2124*f*.

It is further noted that FIGS. 19-21 may depict example simulated results at stage 1534 of example process 1500 (FIG. 15).

Damage Accumulation to Predict Breaking

Figure 22:
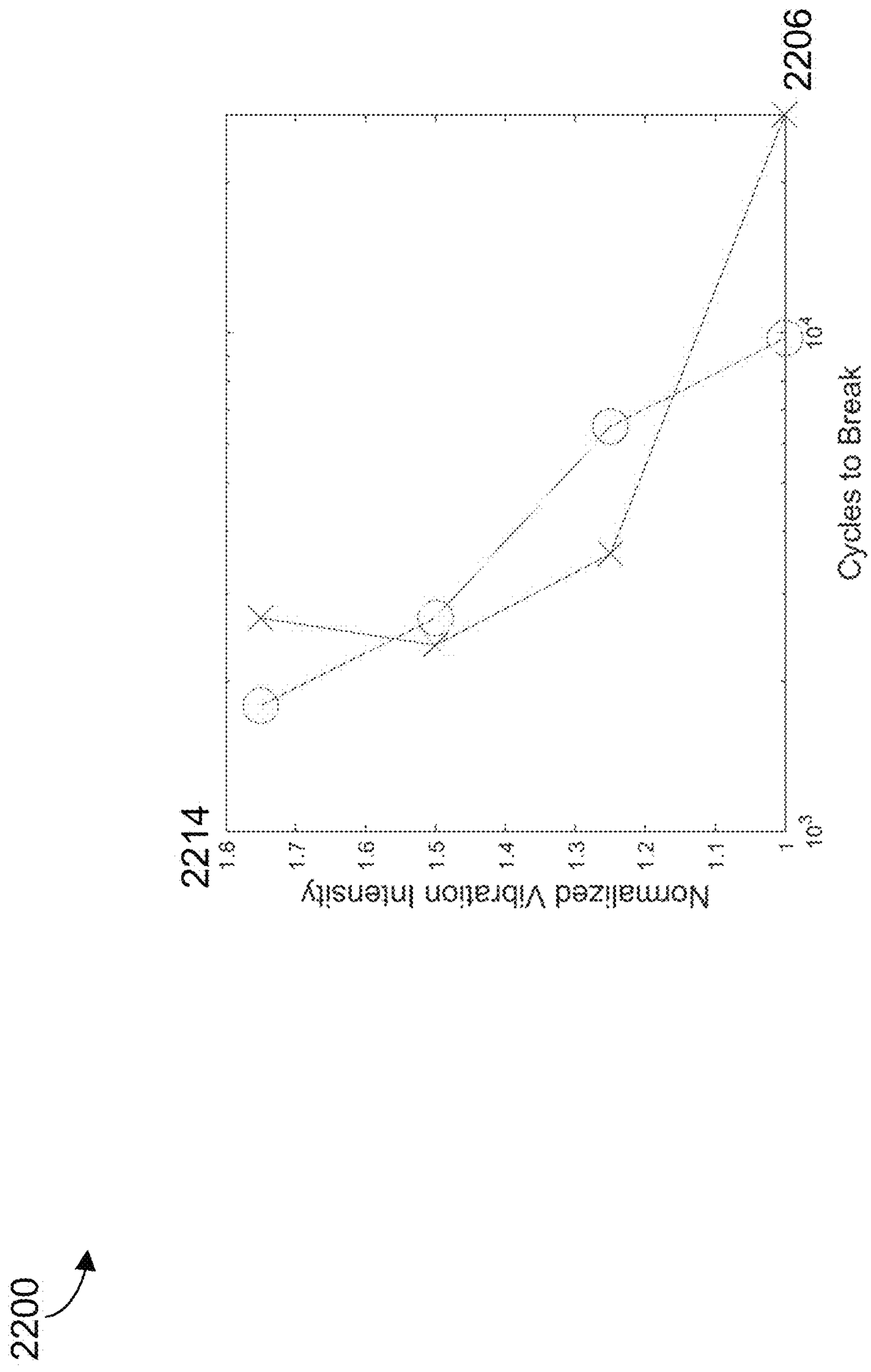
FIG. 22 is an example graph of fatigue represented by normalized vibration intensity over cycles to break.

FIG. 22 is an example graph 2200 of fatigue represented by normalized vibration intensity 2214 over cycles to break 2206. The graph 2200 may also be referred to as a S-N (stress-number of cycles) line. Although FIG. 22 illustrates a S-N line, any other suitable known technique for performing fatigue analysis may also be used.

It is also noted that FIG. 22 may depict example simulated results at stage 1536 of example process 1500 (FIG. 15). As part of stage 1536, graph 2200 of FIG. 22 may be used to relate simulated intensity of vibration (e.g., as shown in FIG. 21) to accumulated damage.

Cover Damage to Decrease Break Time

Figure 23:
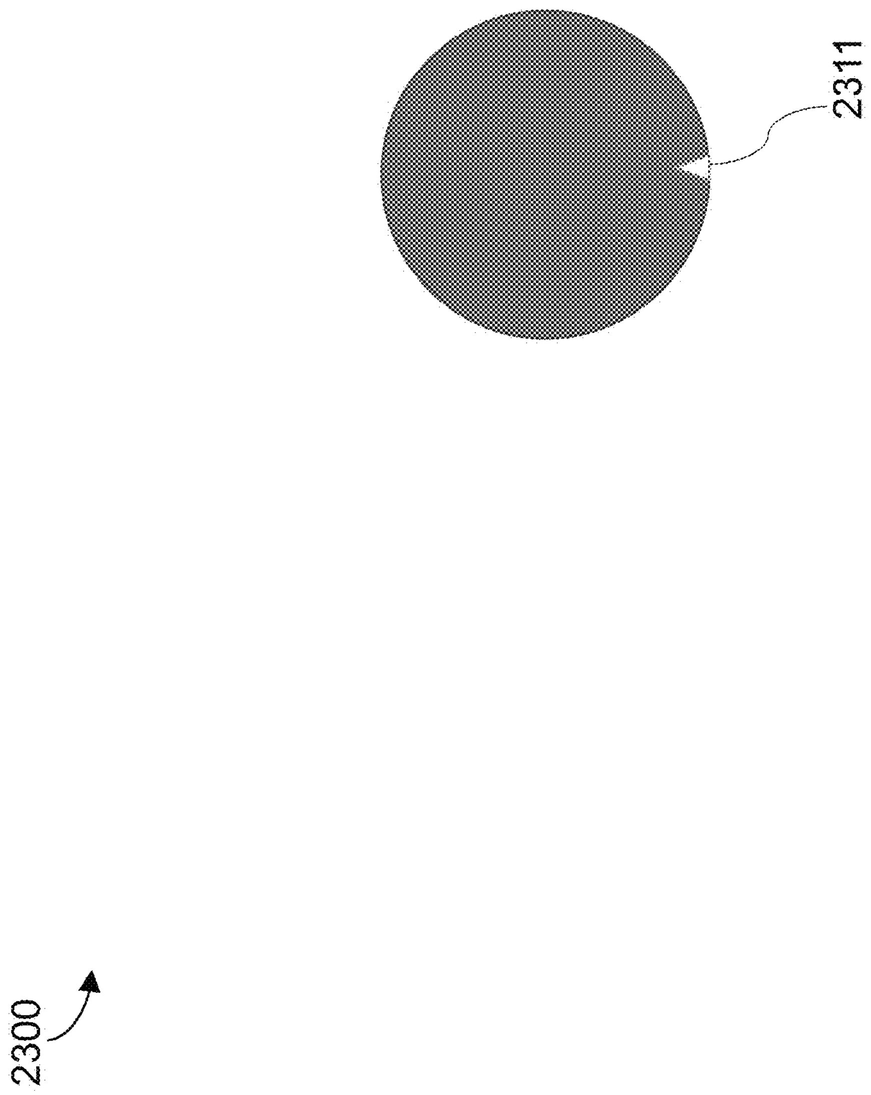
FIG. 23 illustrates an example membrane cover.

FIG. 23 illustrates an example membrane cover 2300. As shown in FIG. 23, a corner 2311 may be etched in cover 2300.

Figure 24:
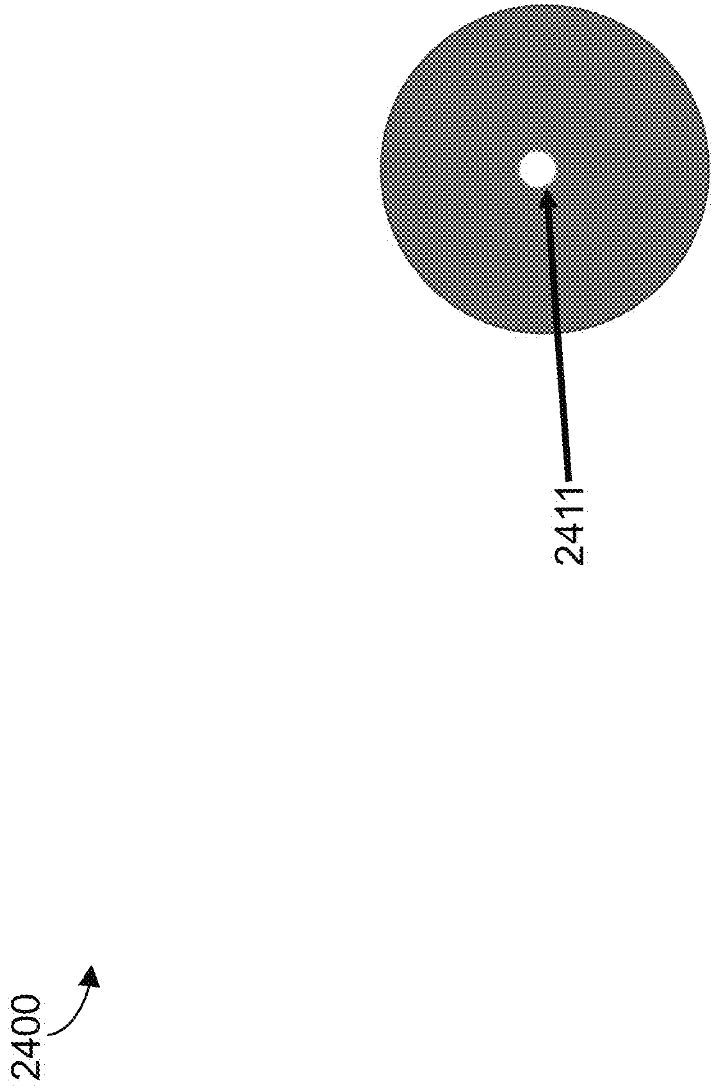
FIG. 24 illustrates another example membrane cover.

FIG. 24 illustrates another example membrane cover 2400. As shown in FIG. 24, pinhole 2411 may be etched in cover 2400. The pinhole 2411 may be a 100 μm pinhole. Other pinhole sizes are also suitable. To continue, pinhole 2411 may be small enough to not allow liquid to pass through membrane 2400.

Figure 25:
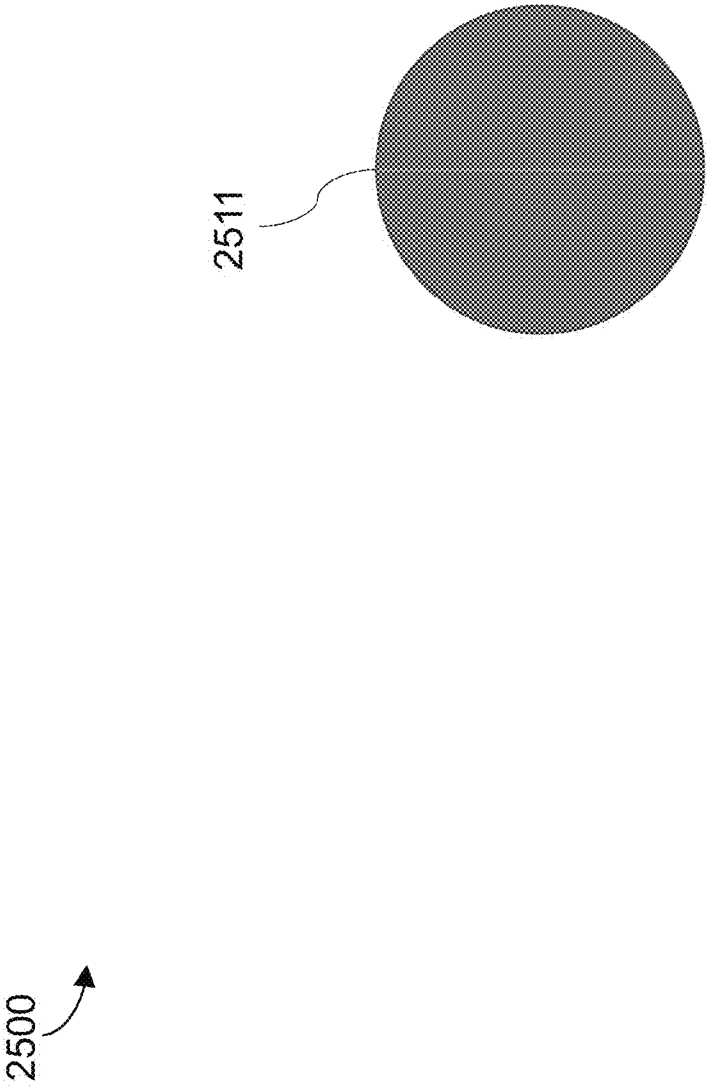
FIG. 25 illustrates yet another example membrane cover.

FIG. 25 illustrates yet another example membrane cover 2500. As shown in FIG. 25, example cover 2500 may include a scored line 2511.

In the context of the present disclosure, creating a weak point, e.g., corner 2311 (FIG. 23), pinhole 2411 (FIG. 24), or scored line 2511 (FIG. 25), in a respective cover, e.g., 2300 (FIG. 23), 2400 (FIG. 24), or 2500 (FIG. 25), may drastically reduce the cover's lifespan. For example, testing results may indicate that using a pinhole, e.g., pinhole 2411, of size 100 μm with a cover, e.g., cover 2400, of diameter 4 mm may reduce the cover's lifespan by roughly 90%. To continue, other damage, such as etching out a corner, e.g., 2311, or scoring a line, e.g., 2511, in a membrane cover may be used to decrease the cover's lifespan and change its breaking behavior. Further, a corner, e.g., 2311, or pinhole, e.g., 2411, may be small enough to not allow liquid to pass through a respective membrane, e.g., 2300 or 2400.

Two-Well Opening (Arbitrary Order)

FIGS. 26A-E are example images 2600*a-e* of test results for spatial resolution ability of a sensor array using a two-well device.

Figure 26A:
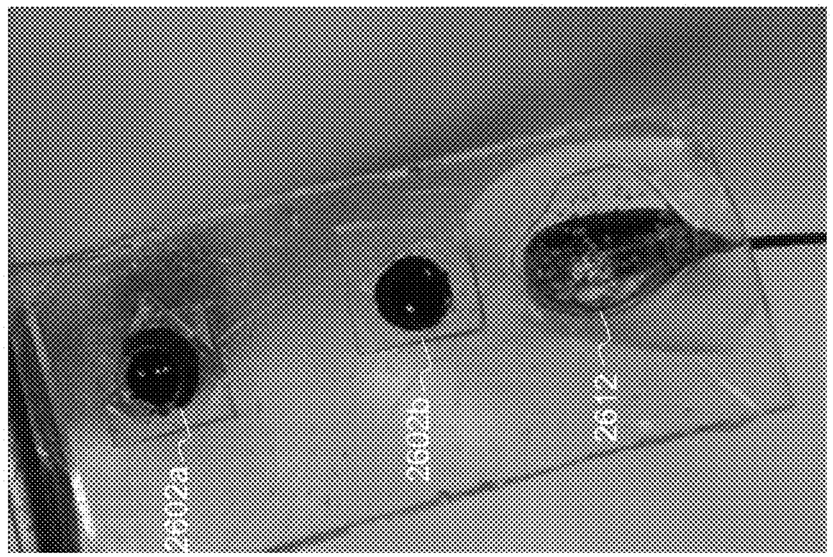
FIGS. 26A-E are example images of test results for spatial resolution ability of a sensor array using a two-well device.

FIG. 26A is an example image 2600*a* of a device with two wells 2602*a-b* and motor 2612. As shown in image 2600*a*, covers of both wells 2602*a-b* are unbroken.

Figure 26B:
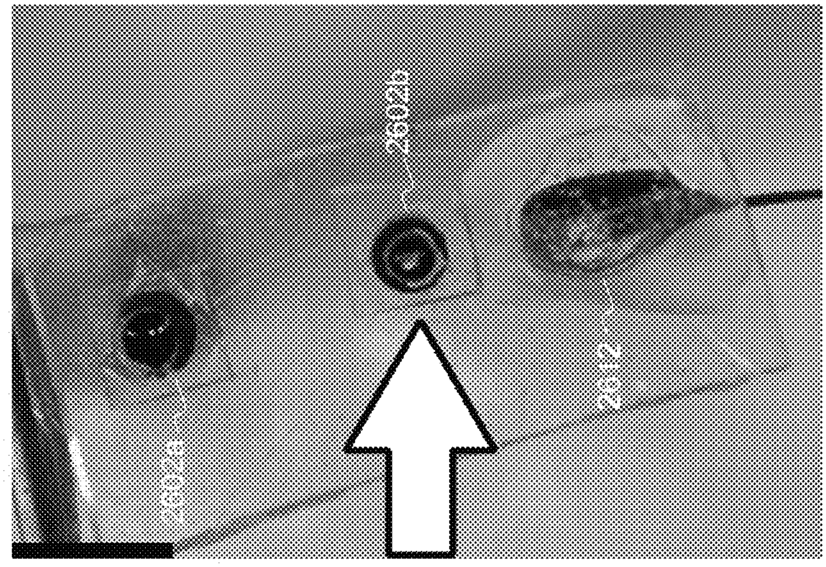

FIG. 26B is a second example image 2600*b* of the device with two wells 2602*a-b*. As shown in FIG. 26B, when an input voltage of 2 V is applied to motor 2612 for 4 s, a cover of well 2602*b* nearest to motor 2612 may break, as indicated with blue dye in well 2602*b*.

Figure 26C:
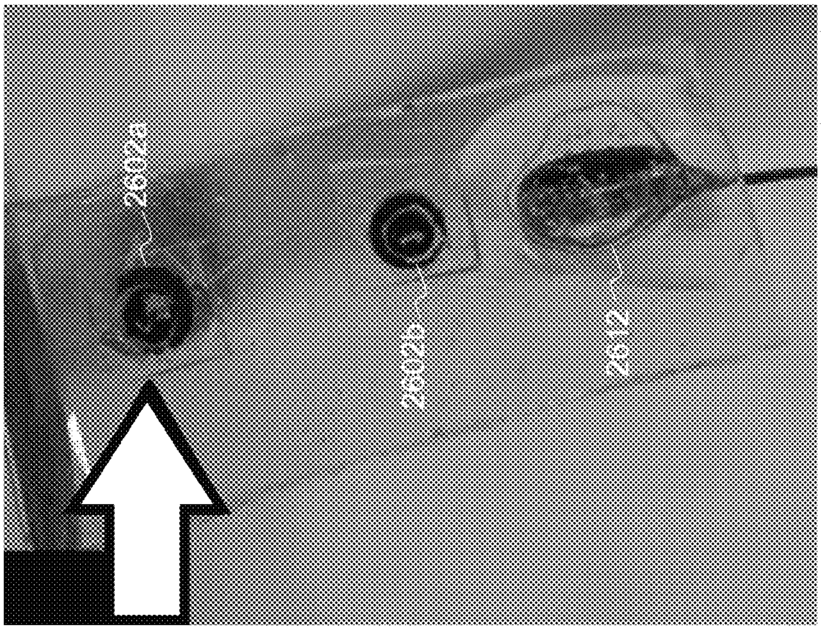

FIG. 26C is a third image 2600*c* of the device with two wells 2602*a-b*. As shown in FIG. 26C, when an input voltage of 4 V is applied to motor 2612 for 2 s, a cover of well 2602*a* farthest from motor 2612 may break, as indicated with red dye in well 2602*a*.

Figure 26D:
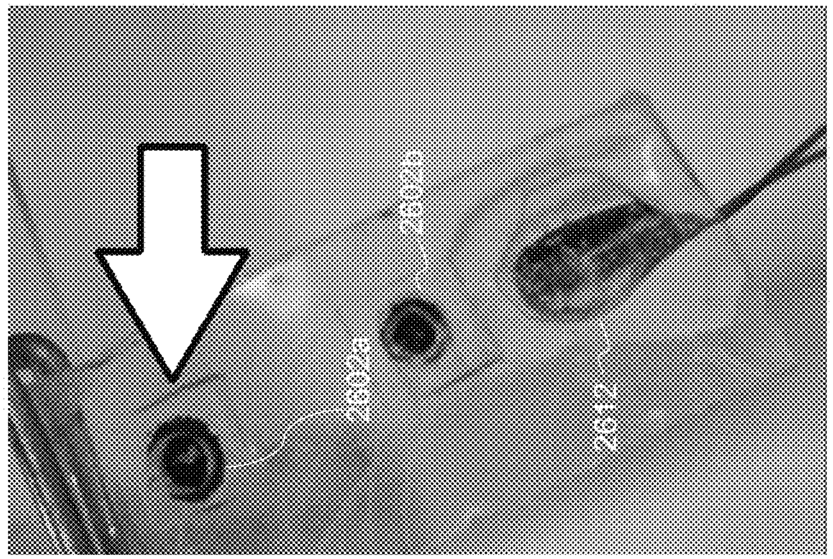

FIG. 26D is a fourth example image 2600*d* of the device with two wells 2602*a-b*. As shown in FIG. 26D, when an input voltage of 4 V is applied to motor 2612 for 7 s, a cover of well 2602*a* farthest from motor 2612 may break, as indicated with red dye in well 2602*a*.

Figure 26E:
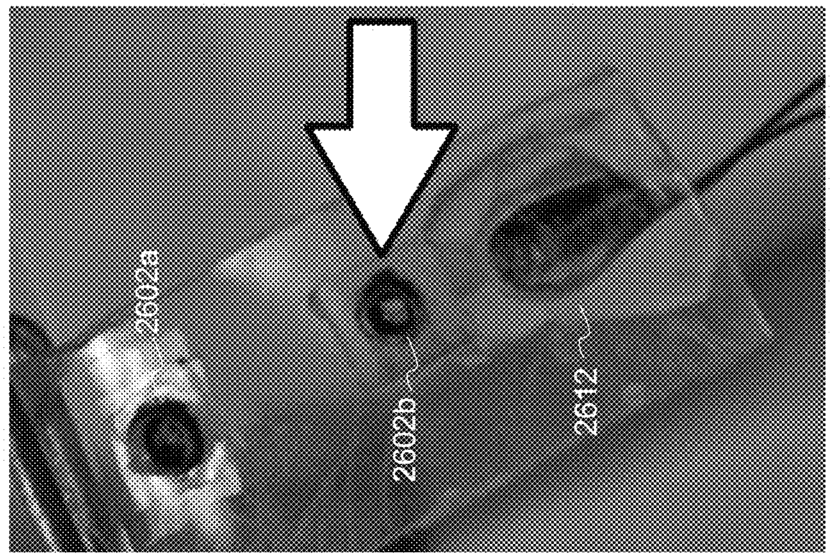

FIG. 26E is a fifth example image 2600*b* of the device with two wells 2602*a-b*. As shown in FIG. 26E, when an input voltage of 2 V is applied to motor 2612 for 30 s, a cover of well 2602*b* nearest to motor 2612 may break, as indicated with blue dye in well 2602*b*.

In the context of the present disclosure, a well, e.g., 2602*b*, closer to a motor, e.g., 2612, may have a pinhole, e.g., 2411 (FIG. 24), in its cover, e.g., 2400 (FIG. 24), to decrease break time of the well's cover.

Four-Well Opening (Single Order)

Figure 27:
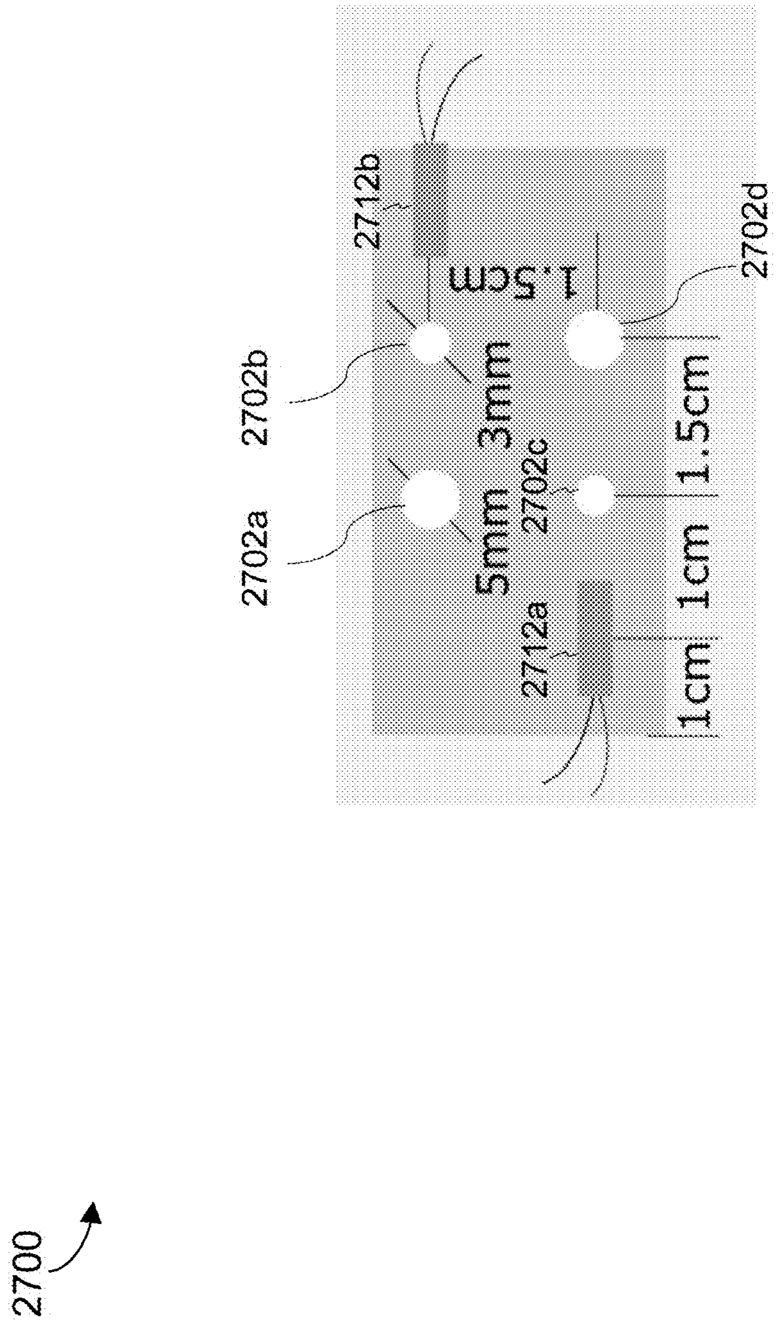
FIG. 27 illustrates an example device including four wells and two motors.

FIG. 27 illustrates an example device 2700 including four wells 2702*a-d* and two motors 2712*a-b*.

FIGS. 28A-E are example images 2800*a-e* of test results for spatial resolution ability of a sensor array using a four-well device, e.g., device 2700 (FIG. 27).

Figure 28A:
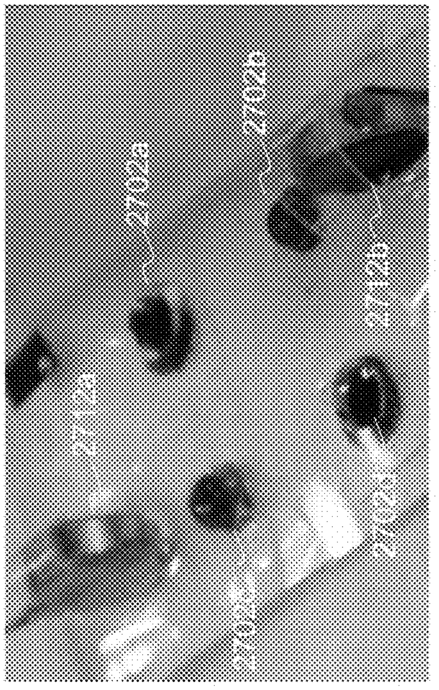
FIGS. 28A-E are example images of test results for spatial resolution ability of a sensor array using a four-well device.

FIG. 28A is an example image 2800*a* of the device 2700 of FIG. 27. As shown in image 2800*a*, covers of all wells 2702*a-d* are unbroken.

Figure 28B:
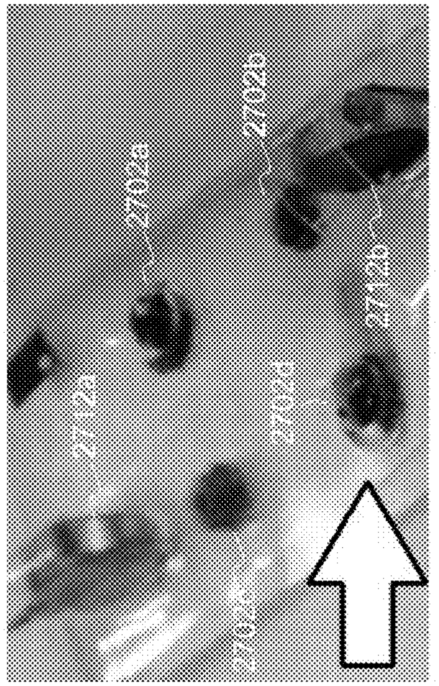

FIG. 28B is a second example image 2800*b* of the device 2700 of FIG. 27. As shown in FIG. 28B, when an input voltage of 2.6 V is applied to motor 2712*a* for ~10 s, a cover of well 2702*d* may break, as indicated by release of red dye on well 2702*d*.

Figure 28C:
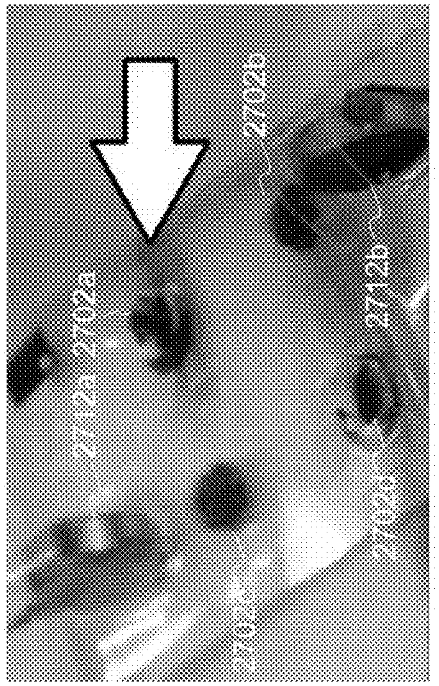

FIG. 28C is a third example image 2800*c* of the device 2700 of FIG. 27. As shown in FIG. 28C, when the input voltage of 2.6 V is applied to motor 2712*a* for a further ~19 s, a cover of well 2702*a* may break, as indicated by release of red dye on well 2702*a*.

Figure 28D:
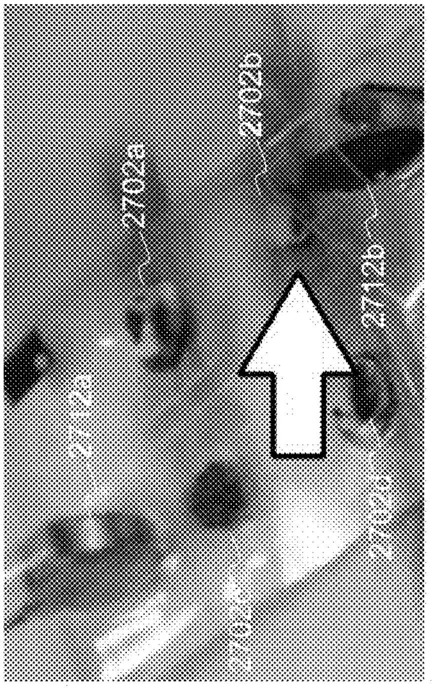

FIG. 28D is a fourth example image 2800*d* of the device 2700 of FIG. 27. As shown in FIG. 28D, when the input voltage applied to motor 2712*a* is increased to 3 V for ~14 s, a cover of well 2702*b* may break, as indicated by release of red dye on well 2702*b*.

Figure 28E:
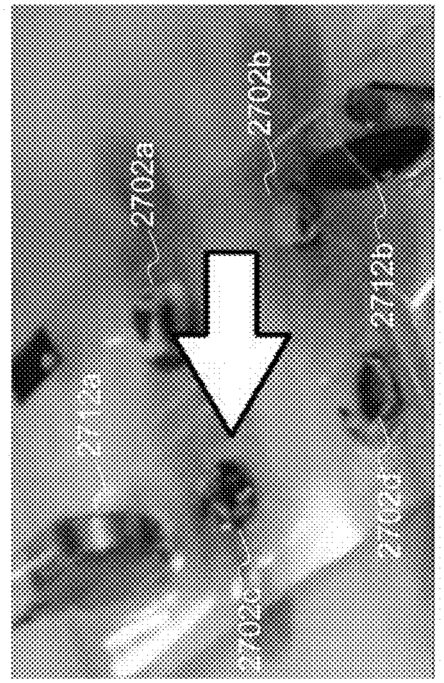

FIG. 28E is a fifth example image 2800*e* of the device 2700 of FIG. 27. As shown in FIG. 28E, when the input voltage of 4 V is applied to motor 2712*a* for a further ~33 s, a cover of well 2702*c* may break, as indicated by release of red dye on well 2702*c*.

Sensor Readings During/After Opening

Figure 29A:
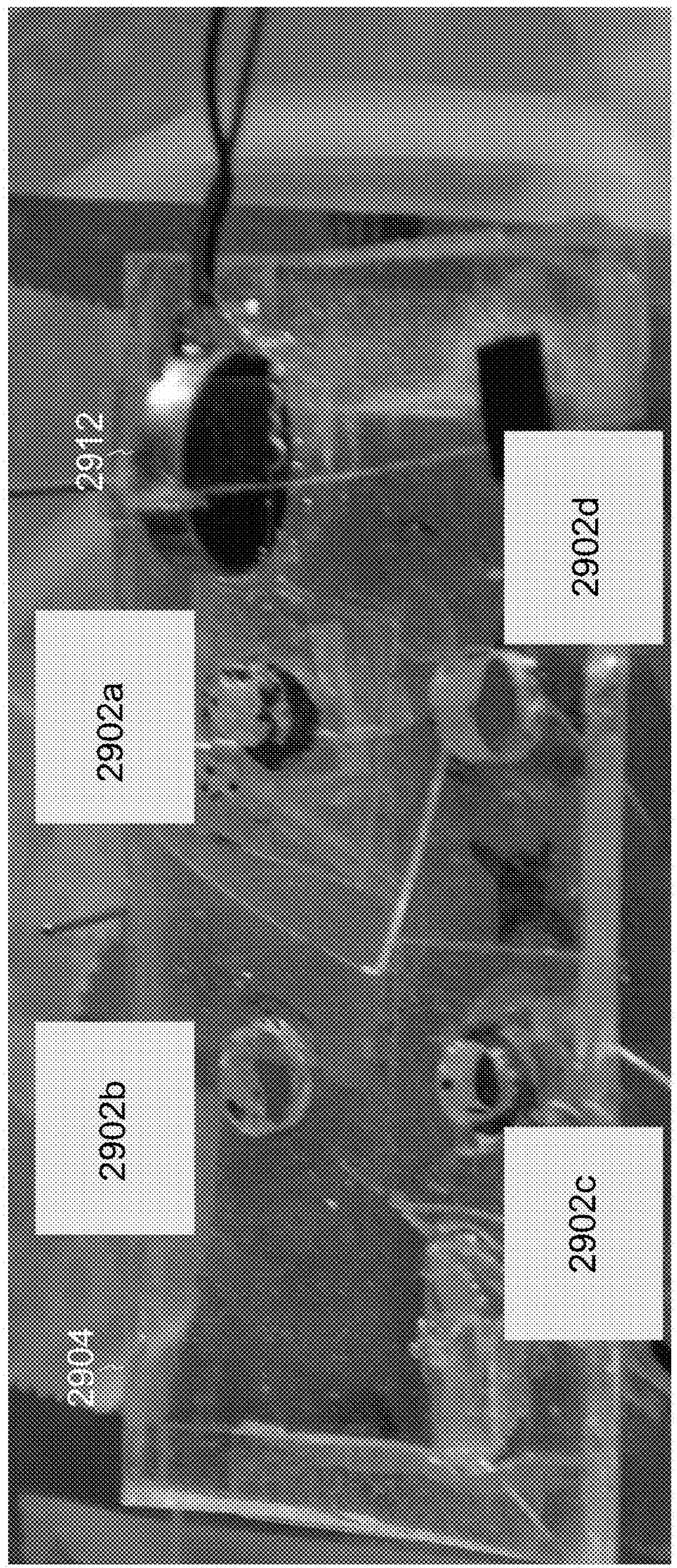
FIG. 29A is an image of an example device.

FIG. 29A is an image of an example device 2900 including substrate 2904, wells 2902*a-d*, and motor 2912. The device 2900 may be configured such that only wells 2902*a* and 2902*c* have sensors attached.

Figure 29B:
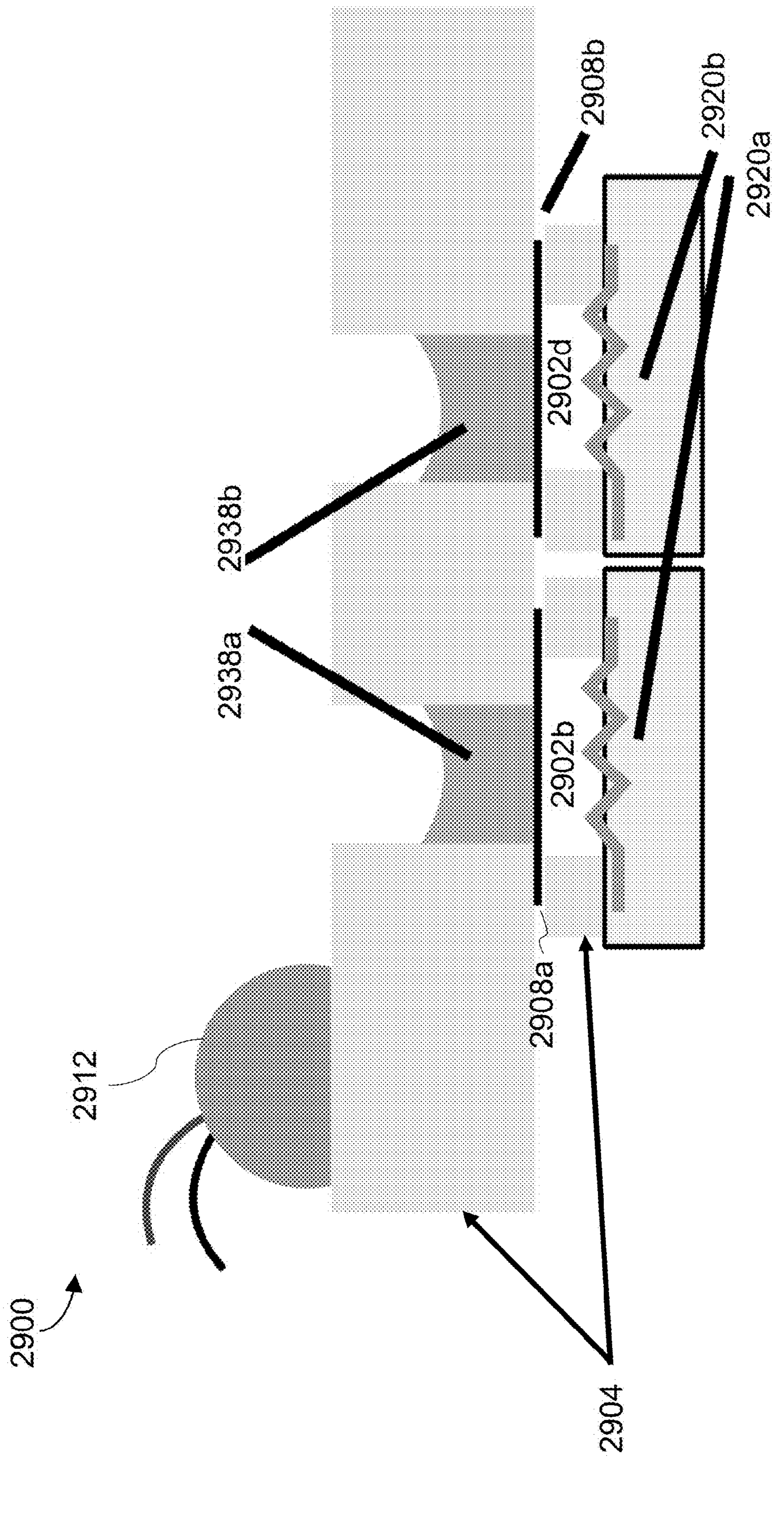
FIG. 29B is a schematic illustration of the device of FIG. 29A.

FIG. 29B is a schematic illustration of the device 2900. As shown in FIG. 29B, in addition to substrate 2904, wells 2902*a-d*, and motor 2912, the well 2902*b* may have sensor 2920*a* and cover 2908*a*, while the well 2902*d* may have sensor 2920*b* and cover 2908*b*. Further, a buffer or solution 2938*a* and 2938*b*, e.g., PBS or any other suitable known buffer or solution, may be loaded initially on covers 2902*a* and 2902*b*, respectively. Lastly, sensors 2920*a* and 2920*b* may be initially exposed to air. Other known gases or mixtures of gases are also suitable.

Figure 30:
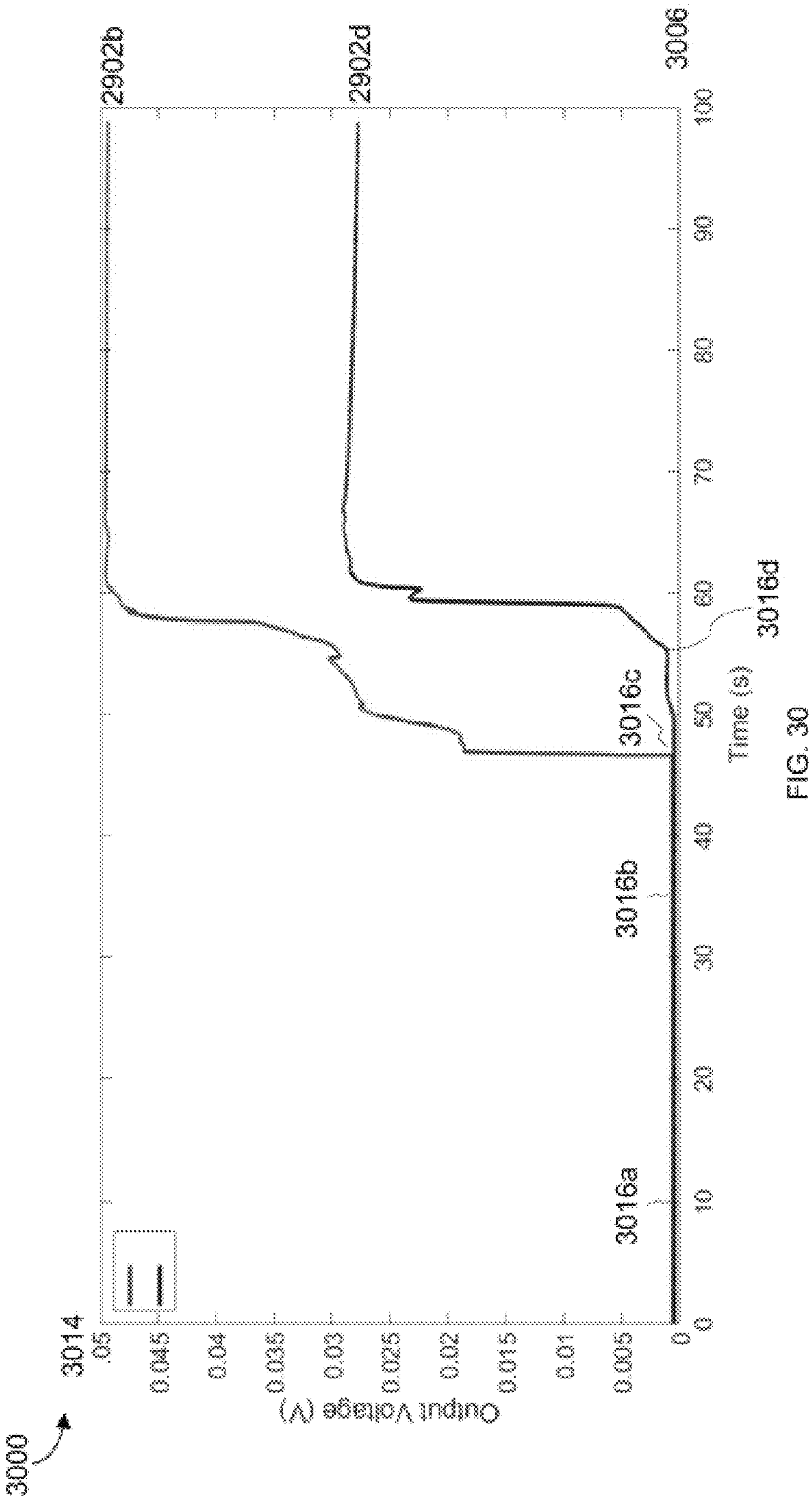
FIG. 30 is an example graph of output voltage over time.

FIG. 30 is an example graph 3000 of output voltage 3014 over time 3006. As shown in FIG. 30, the graph 3000 may depict simulated results for output voltage 3114 of sensors, e.g., sensors 2920*a* and 2920*b* (FIG. 29B) of respective wells 2902*b* and 2902*d* (FIG. 29A), in, for instance, V, over time 3006 in, for instance, s. For example, covers 2908*a* and 2908*b* (FIG. 29B) of respective wells 2902*b* and 2902*d* may be loaded with, e.g., PBS at, for instance, 10 s, as indicated by point 3016*a* and motor 2912 (FIG. 29A) may be given 2.6V at, e.g., 35 s, as indicated by point 3016*b*. To continue, cover 2908*a* of well 2902*b* may break at, e.g., 46 s, as indicated by point 3016*c*, followed by cover 2908*b* of well 2902*d* breaking at, e.g., 55 s, as indicated by point 3016*d*.

Alternate Cover Geometry

Figure 31:
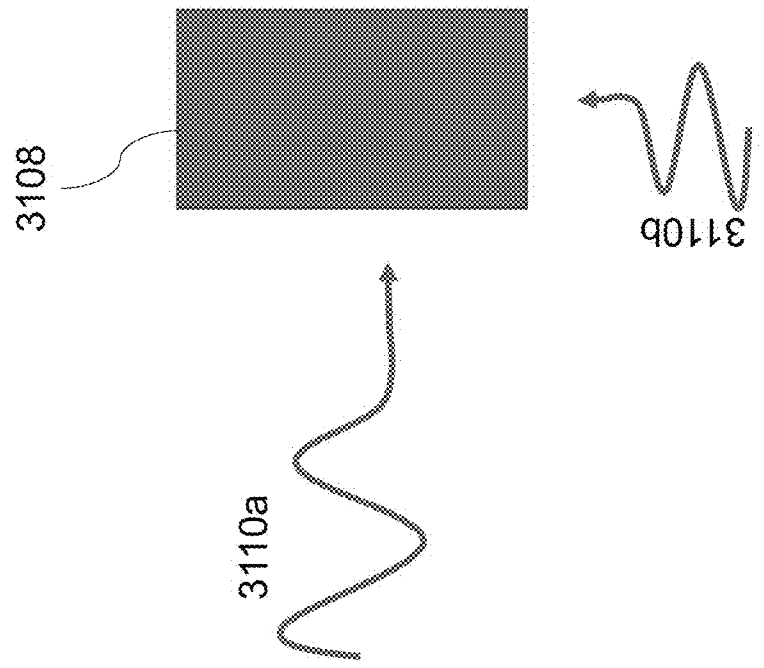
FIG. 31 illustrates an example cover.

FIG. 31 illustrates an example cover 3108. As shown in FIG. 31, cover 3108 may be rectangularly-shaped. In the context of the present disclosure, different shaped covers, e.g., rectangularly-shaped cover 3108, may exhibit separate frequency responses and resonances corresponding to various frequencies, e.g., frequency 3110*a* or 3110*b* of FIG. 31. Such differential frequency responses and resonances may support new options for using multiple motors to expand an array of controllable covers.

As used herein, the "selective" rupture of a membrane means that a vibration supplied by an actuator of the device is specific to effecting the rupture of the membrane at its specific location within the array, such as by an intended timing and/or an intended order of rupture among the several wells of the array.

An advantage of the configuration shown in FIG. 3 is that one actuator can be used to control the ordered opening of several wells in an array, thus reducing complexity of the device. A single actuator can provide for reduced size, weight, wiring, and/or power requirements. A single-actuator configuration may be desirable where the device is to have a small footprint. Devices can alternatively include two or more actuators. Multiple actuators can be included where larger arrays are provided and/or to provide for increased flexibility and specificity in effecting membrane rupture within the device. The inclusion of, for example, two actuators within a device can provide for similar advantages as single-actuator devices. In particular, vibratory patterns can be provided by the two actuators to effect selective rupture of membranes of a large array, providing for scalability while still providing for reduced size, weight, wiring, and/or power requirements.

The membrane can comprise a material that is durable for the purposes of maintaining a barrier between a tissue and a well of the device while also providing for responsiveness to vibrations. For example, the membrane can be or include a thin sheet of liquid-proof material configured to resonate at a defined frequency. Examples of suitable membrane materials include graphene oxide, polymer thin film, metal, ceramic, cellulose paper, or a combination thereof.

The substrate can comprise a material capable of defining an array of wells and capable of permitting vibrations applied by the actuator to travel throughout the substrate. It can be advantageous for the substrate to comprise a biocompatible material. An example of a substrate material is PDMS. Other polymers and materials can also be suitable.

An example device configuration includes a PDMS slab, which is fabricated to define a series of wells, and an embedded vibration motor. The wells can be covered with few-layer GO membranes (e.g., about 10 μm thick). The covers can be ruptured selectively by changing the frequency and amplitude of the vibration supplied by the motor. The well locations can be selected based on simulations of the PDMS slab (e.g., simulations in COMSOL Multiphysics® (COMSOL, Inc., Burlington, MA)), while the diameter and thickness of the GO membranes are simulated for matching frequencies and amplitude response. Such a configuration can provide for selective breaking of well "covers" (i.e., membranes) based on input frequency and amplitude of vibration.

Devices can include additional, optional features, such as porous membranes to prevent well contents from being released into tissue and micro-channels to assist with fluid guidance into wells.

A well shape and size, as well as a membrane shape, size, and/or material characteristics can be selected to provide for an intended response. For example, wells and/or membranes can be of circular cross-sectional shapes, or may be of other shapes such that the wells and/or membranes are adapted to respond to not only a frequency of a vibration but also a direction of the vibration. The wells and/or membranes can be, for example, rectangularly-shaped, triangularly-shaped, circularly-shaped, polygonal-shaped, or oblong-shaped. The membranes can optionally include structural features, such as etching or scores, to decrease breaking time.

Where more than one actuator is included, wells and/or membranes can be configured to respond differently to a vibration supplied by each motor depending upon an orientation and/or direction of the supplied vibration.

The wells can include sensors for biomarker detection. Examples of such sensors include impedance sensors, such as impedance sensors including functionalized surfaces (e.g., antigens immobilized at a sensor surfaces) and/or molecularly imprinted polymers. Examples of multi-well impedance sensors are further described in "Transcutaneous Wearable Apparatus for Continuous Monitoring of Biomarkers in Blood," published as WO 2019/190596, the entire contents of which are incorporated herein by reference.

The wells can include a therapeutic substance, such as a drug, an ointment, or the like. For example, the wells can contain wound healing accelerators, growth factors, and debriding agents.

The provided devices and methods can be used in a variety of applications, including, for example, continuous or periodic biosensing, which can provide for real-time measurement of biomarkers, and closed-loop drug delivery. For example, the device can be or can be included in a "smart bandage" to deliver a therapeutic substance in a controlled, timed manner. Optionally, the device can be used for multiple, concurrent applications. For example, operation of the actuator can be at least partially informed by sensing results. The use of vibration to break membranes separating a sensor from a sample to be analyzed can allow for the release of medication from the same well, or from a different well. For example, a subset of the wells of the array can be drug-delivery wells, and a subset can be sensing wells. Depending upon an analyte concentration detected by a sensor of a ruptured-membrane well, the actuator can supply a vibration suitable for breaking a distinct well containing a drug. Alternatively, or in addition, an analyte concentration detected by a sensor of a ruptured-membrane well can inform timing of a next membrane to be ruptured.

The teachings of all patents, published applications, and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A device to selectively access tissue for sensing or drug release, the device comprising:

an array of wells formed in a substrate supporting a plurality of membranes, each membrane disposed at a well opening of one of the wells of the array;

an actuator; and electronics configured to control the actuator to supply a vibration through the substrate, the supplied vibration selectively rupturing one of the plurality of membranes at a defined timepoint to selectively give access to tissue through a well opening.

2. The device of claim 1, wherein the rupturing of one of the plurality of membranes includes breaking an interface between the tissue and a well associated with the well opening.

3. The device of claim 1, wherein the supplied vibration causes the plurality of membranes to accumulate different degrees of damage over time.

4. The device of claim 1, wherein the plurality of membranes comprises a material including graphene oxide, polymer thin film, metal, ceramic, cellulose paper, or a combination thereof.

5. The device of claim 1, wherein each of the plurality of membranes comprises a sheet of liquid-proof material configured to resonate at a defined frequency when exposed to the vibration.

6. The device of claim 1, wherein the plurality of membranes comprises differently-shaped membranes adapted to respond to the vibration at different resonances.

7. The device of claim 1, wherein the plurality of membranes comprises membranes of a shape adapted to respond to the vibration according to a frequency and direction of the vibration.

8. The device of claim 7, wherein the membranes are rectangularly-shaped, triangularly-shaped, circularly-shaped, polygonal-shaped, or oblong-shaped.

9. The device of claim 1, further comprising plural actuators supplying vibrations having different frequencies, originating from different directions with respect to the array, or a combination thereof.

10. The device of claim 1, further comprising an external power source configured to drive the electronics, the actuator, or both.

11. The device of claim 1, further comprising a porous membrane covering each membrane.

12. The device of claim 1, further comprising a plurality of micro-channels, each micro-channel associated with one of the wells of the array and configured to guide fluid into the well from the tissue.

13. The device of claim 1, further comprising a drug, a sensor, or combination thereof encapsulated in at least one of the wells.

14. The device of claim 1, wherein at least a portion of the substrate is configured to be (i) positioned at a biological surface or (ii) implanted into a biological tissue.

15. A method for selectively accessing tissue for sensing or drug release, the method comprising:

providing an array of wells formed in a substrate supporting a plurality of membranes, each membrane disposed at a well opening of one of the wells; and controlling an actuator to supply a vibration through the substrate, the supplied vibration selectively rupturing one of the plurality of membranes at a defined timepoint to selectively give access to tissue through a well opening.

16. The method of claim 15, wherein the rupturing of one of the plurality of membranes includes breaking an interface between the tissue and a well associated with the well opening.

17. The method of claim 15, wherein supplying the vibration to the substrate comprises providing varying degrees of accumulated damage over time to each of the plurality of membranes.

18. The method of claim 15, wherein supplying the vibration to the substrate comprises supplying the vibration according to a frequency, a direction, or a combination thereof for the selective rupture of the one of the plurality of membranes.

19. The method of claim 15, further comprising preventing debris from the rupture of the one of the plurality of membranes from reaching the tissue.

20. The method of claim 15, further comprising guiding fluid from tissue into a well associated with the well opening via a micro-channel.

21. The method of claim 15, further comprising exposing the tissue to a drug encapsulated in a well associated with the well opening, exposing a sensor encapsulated in the well associated with the well opening to fluid from the tissue, or a combination thereof.

22. The method of claim 15, further comprising positioning at least a portion of the substrate at a biological surface or implanting at least a portion of the substrate into a biological tissue.

* * * * *